United States Patent [19]

Daniels et al.

[11] 4,044,123

[45] Aug. 23, 1977

[54] 6'-N-ALKYL-4,6-DI-O-(AMINOGLYCOSYL)-1,3-DIAMINOCYCLITOLS, METHODS FOR THEIR USE AS ANTIBACTERIAL AGENTS AND COMPOSITIONS USEFUL THEREFOR

[75] Inventors: Peter J. L. Daniels, Cedar Grove; William N. Turner, Bloomfield, both of N.J.

[73] Assignee: Schering Corporation, Kenilworth, N.J.

[21] Appl. No.: 666,715

[22] Filed: Mar. 15, 1976

Related U.S. Application Data

[63] Continuation-in-part of Ser. No. 574,070, May 2, 1975, abandoned.

[51] Int. Cl.$^2$ ................... A61K 31/71; C07H 15/22
[52] U.S. Cl. ............................ 424/180; 424/181; 536/10; 536/17
[58] Field of Search ................. 536/17; 424/180, 181

[56] References Cited

U.S. PATENT DOCUMENTS

| | | |
|---|---|---|
| 3,832,286 | 8/1974 | Weinstein et al. ............... 536/17 |
| 3,925,353 | 12/1975 | Umezawa et al. ............... 536/17 |
| 3,929,762 | 12/1975 | Umezawa et al. ............... 536/17 |
| 3,972,930 | 8/1976 | Daum et al. ..................... 536/17 |

Primary Examiner—Johnnie R. Brown
Attorney, Agent, or Firm—Mary S. King

[57] ABSTRACT

Described are 6'-N-alkyl derivatives of antibacterially active 4,6-di-O-(aminoglycosyl)-1,3-diaminocyclitols having a primary carbinamine at C-5' of which a preferred group are 6'-N-alkyl derivatives having 2 to 4 carbon atoms of 4-O-aminoglycosyl-6-O-garosaminyl-2-deoxystreptamines having a primary carbinamine at C-5', a particularly preferred compound being 6'-N-ethylsisomicin.

The 6'-N-alkyl derivatives are prepared by the reaction of the corresponding 6'-N-unsubstituted aminoglycoside having protecting groups on all other amino functions with an aldehyde or a ketone, followed by the reaction in situ of the 6'-N-substituted intermediate thereby formed with a hydride reducing agent, then removal of any N-protecting groups.

Pharmaceutical formulations comprising 6'-N-alkylaminoglycosides of the invention are described and the method for their use in treating bacterial infections.

15 Claims, No Drawings

6'-N-ALKYL-4,6-DI-O-(AMINOGLYCOSYL)-1,3-DIAMINOCYCLITOLS, METHODS FOR THEIR USE AS ANTIBACTERIAL AGENTS AND COMPOSITIONS USEFUL THEREFOR

CROSS REFERENCE TO RELATED APPLICATIONS

This application is a continuation-in-part of co-pending application U.S. Ser. No. 574,070 filed May 2, 1975, now abandoned.

FIELD OF INVENTION

This invention relates to novel compositions-of-matter, to methods for their manufacture, to pharmaceutical formulations and to methods for their use as antibacterial agents.

More specifically, this invention relates to novel 6'-N-alkyl-4,6-di-0-(aminoglycosyl)-1,3-diaminocyclitols having a primary carbinamine at C-5' which exhibit antibacterial activity, to methods for their manufacture, to pharmaceutical compositions comprising said 6'-N-alkyl-4,6-di-O-(aminoglycosyl)-1,3-diaminocyclitols and to methods for their use in treating bacterial infections.

In particular, this invention relates to 6'-N-alkyl derivatives of 4,6-di-O-(aminoglycosyl)-2-deoxystreptamine antibacterial agents having a primary carbinamine at C-5' including sisomicin, Antibiotics 66-40B and 66-40D; and to 6'-N-alkyl derivatives of related 4,6-di-O-(aminoglycosyl)-1,3-diaminocyclitol antibacterial agents such as the 5-epi-, the 5-epi-amino-5-deoxy- and the 5-epi-azido-5-deoxy- analogs of the foregoing and of gentamicins $C_{1a}$ and B and of Antibiotic JI-20A; and also including antibacterial agents such as Antibiotics Mu-1, Mu-2, Mu-4 and Mu-5. The 6'-N-alkyl derivatives of this invention include 6'-N-alkyl, 6'-N-alkenyl, 6'-N-cycloalkylakyl, 6'-N-hydroxyalkyl, 6'-N-aminoalkyl, 6'-alkylaminoalkyl, 6'-N-aminohydroxyalkyl, and 6'-N-alkylaminohydroxyalkyl derivatives.

This invention also relates to processes for preparing the foregoing 6'-N-alkyl-4,6-di-0-(aminoglycosyl)-1,3-diaminocyclitols, to pharmaceutical compositions comprising said 6'-N-alkyl-4,6-di-O-(aminoglycosyl)-1,3-diaminocyclitols, and to the method of using said pharmaceutical compositions to elicit an antibacterial response in a warm blooded animal having a susceptible bacterial infection.

PRIOR ART

Known in the art are broad spectrum antibacterial agents which may be classified chemically as 4,6-di-O-(aminoglycosyl)-1,3-diaminocyclitols. Of this group, those wherein the aminoglycosyl group at the 6-position is a garosaminyl radical are valuable antibacterial agents, particularly those wherein the 1,3-diaminocyclitol is 2-ceoxystreptamine. Within this class of 4-O-aminoglycosyl-6-O-garosaminyl-2-deoxystreptamines, those having a primary carbinamine at C-5' include antibiotics such as gentamicins $C_{1a}$ and B, sisomicin, and Antibiotic JI-20A. Related 4-O-aminoglycosyl6-O-garosaminyl-1,3-diaminocyclitols having a primary carbinamine at C-5' include the 5-epi-, 5-epi-amino-5-deoxy- and the 5-epiazido-5-deoxy analogs of the foregoing as well as Antibiotics Mu-1, Mu-2, Mu-4 and Mu-5. Other 4,6-di-O-(aminoglycosyl)-1,3-diaminocyclitols having a primary carbinamine at C-5' are Antibiotics 66-40B and 66-40D and the 5-epi-, 5-epi-amino-5-deoxy and the 5-epi-azido-5-deoxy- analogs thereof.

Also described in the art are 6'-N-methyl derivatives of kanamycin and of 3',4'-dideoxykanamycin B prepared by reduction of the corresponding 6'-N-benzyloxycarbonylkanamycin or 6'-N-benzyloxycarbonyl-3',4'-dideoxykanamycin B with lithium aluminum hydride. By this process there can be prepared only 6'-N-methyl aminoglycoside derivatives.

In addition to the foregoing, known are some antibiotics which are 6'-N-methyl derivatives of other known 4,6-di-O-(aminoglycosyl)-1,3-diaminocyclitol antibiotics, both of which are produced microbiologically. Thus, Antibiotic G-52 (which is 6'-N-methylsisomicin) is produced via the fermentation under aerobic conditions of *Micromonospora zionensis;* while gentamicin $C_{2b}$ (which is 6'-N-methylgentamicin $C_{1a}$ and which has also been named in some prior art as gentamicin $C_{2a}$) is produced by the fermentation under aerobic conditions of *Micromonospora purpurea NRRL* 2953.

Additionally, in South African Pat. No. 73/7780 (the invention of which is also described in co-pending U.S. Application Ser. No. 596,799 filed July 17, 1975 of Alan K. Mallams for *Garamine and Novel Derivatives Thereof*) there is generically disclosed 6'-N-alkyl derivatives of gentamicins $C_{1a}$ and B and of Antibiotic JI-20A and a method for their preparation by reaction of a selectively blocked garamine with a monosaccharide.

By our invention, we have discovered a method of preparing 6'-N-alkyl derivatives of 4,6-di-O-(aminoglycosyl)1,3-diaminocyclitols having a primary carbinamine at C-5', said alkyl having at least two carbon atoms, which derivatives cannot be prepared by any of the aforementioned prior art processes. Moreover, by our invention, it has been discovered that such 6'-N-alkyl derivatives of said 4,6-di-O-(aminoglycosyl)-1,3-diaminocyclitol having a primary carbinamine at C-5', are broad spectrum antibacterial agents which are active against strains resistant to the parent antibiotics. Preferred compounds are 6'-N-ethyl derivatives, particularly 6'-N-ethylsisomicin.

GENERAL DESCRIPTION OF THE INVENTION COMPOSITION-OF-MATTER ASPECT

Included among the antibacterially active compositions-of-matter of this invention are 6'-N-X-4,6-di-O-(aminoglycosyl)-1,3-diaminocyclitols selected from the group consisting of 6'-N-X-sisomicin,
6'-N-X-Antibiotic 66-40B,
6'-N-X-Antibiotic 66-40D,
6'-N-X-Antibiotic Mu-1,
6'-N-X-Antibiotic Mu-2,
6'-N-X-Antibiotic Mu-4,
6'-N-X-Antibiotic Mu-5, and
the 5-epi-, 5-epi-amino-5-deoxy-, and the 5-eip-azido-5-deoxy- analogs of the following:
6'-N-X-gentamicin $C_{1a}$,
6'-N-X-gentamicin B,
6'-N-X-Antibiotic JI-20A,
6'-N-X-Antibiotic 66-40B,
6'-N-X-Antibiotic 66-40D,
6'-N-X-sisomicin,
wherein X is an alkyl substituent selected from the group consisting of alkyl, cycloalkylalkyl, alkenyl, hydroxyalkyl, aminoalkyl, alkylaminolkyl, aminohydroxyalkyl and alkylaminohydroxyalkyl, said substituent having two to eight carbon atoms, the carbon in said substituent adjacent to the aminoglycoside nitrogen being primary or secondary and unsubstituted by hydroxyl or amino functions, and when said substituent is substituted by both hydroxyl and amino functions only one of said functions can be attached at any one carbon atom;

and the pharmaceutically acceptable acid addition salts thereof.

Included among the alkyl substituents contemplated for the moiety X in our novel compounds are straight and branched chain alkyl groups such as ethyl, n-propyl, n-butyl, β-methylpropyl, n-pentyl, β-methylbutyl, γ-methylbutyl and β,β-dimethylpropyl; n-hexyl, δ-methylpentyl, β-ethylbutyl, γ-ethylbutyl, n-heptyl, ε-methylheptyl, β-ethylpentyl, γ-ethylpentyl, δ-ethylpentyl, γ-propylbutyl, n-octyl, iso-octyl, β-ethylhexyl, δ-ethylhexyl, ε-ethylhexyl, β-propylpentyl, γ-propylpentyl; alkenyl groups such as β-propenyl, β-methylpropenyl, β-butenyl, β-methyl-β-butenyl, β-ethyl-β-hexenyl; cycloalkylalkyl groups such as cyclopropylmethyl, cyclopentylmethyl, cyclohexylethyl and cyclopentylethyl; hydroxy substituted straight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl, ω-hydroxyoctyl; amino substituted straight and branched chain alkyl groups such as ε-aminopentyl, β-aminopropyl, γ-aminopropyl, δ-aminobutyl, β-amino-γ-methylbutyl and ω-aminooctyl and mono-N-alkylated derivatives thereof such as the N-methyl, N-ethyl, and N-propyl derivatives, e.g. ε-methylaminopentyl, β-methylaminopropyl, β-ethylaminopropyl, δ-methylaminobutyl, β-methylamino-γ-methylbutyl, and ω-methylaminobutyl; amino and hydroxy disubstituted straight and branched chain alkyl groups such as β-hydroxy-ε-aminopentyl, γ-hydroxy-γ-methyl-δ-aminobutyl, β-hydroxy-δ-aminobutyl, β-hydroxy-γ-aminopropyl, and β-hydroxy-β-methyl-γ-aminopropyl; and mono-N-alkylated derivatives thereof such as β-hydroxy-εmethylaminopentyl, γ-hydroxy-γ-methyl-δmethylaminobutyl, β-hydroxy-δ-methylaminobutyl, β-hydroxy-γ-ethylaminopropyl, and β-hydroxy-β-methyl-γ-methylaminopropyl.

Of the foregoing alkyl substituents contemplated for the moiety X, preferred are lower alkyl substituents having 2 to 4 carbon atoms, particularly valuable derivatives being 6'-N-ethyl-4,6-di-O-(aminoglycosyl)-1,3-diaminocyclitols, e.g. 6'-N-ethylsisomicin.

Our compounds are preferably 6'-N-X-derivatives containing the 1,3-diaminocyclitol known as 2-deoxystreptamine, said 2-deoxystreptamine being present in all the above listed compounds of our invention except in the 5-epi-, the 5-epi-amino5-deoxy- and the 5-epi-azido-5-deoxy- analogs, and in 6'-N-X-Antibiotics Mu-1, 2, 4 and 5. The 1,3-diaminocyclitol nucleus in each of the 6'-N-X-Antibiotics Mu-1, 2, 4 and 5 are streptamine, 2,5-dideoxystreptamine, 2-epi-streptamine and 5-amino-2,5-dideoxystreptamine, respectively.

Particularly useful antibacterial agents of our invention are 6'-N-X-4,6-di-O-(aminoglycosyl)-2-deoxystreptamines wherein the aminoglycoside radical at the 6-position is garosaminyl. Typical 6'-N-X-4-O-aminoglycosyl-6-O-garosaminyl-2-deoxystreptamines of this invention include 6'-N-X-sisomicin, which is defined by the following structural formula I:

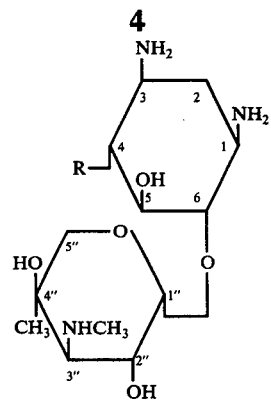

I

R being the following aminoglycosyl:

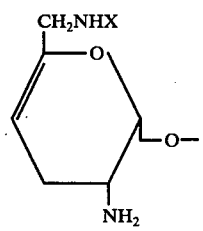

wherein X is as hereinabove defined.

Other useful antibacterial compounds of our invention are 6'-N-X derivatives of Antibiotics 66-40-B and 66-40D, which are defined by the following formula II:

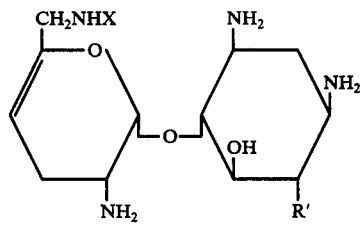

II wherein X is as hereinabove defined, and

R' is an aminoglycosyl function selected from the group consisting of:

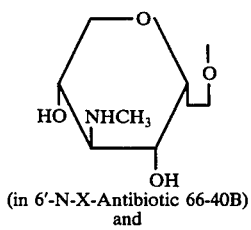

(in 6'-N-X-Antibiotic 66-40B)
and

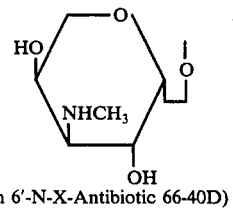

(in 6'-N-X-Antibiotic 66-40D)

Other useful antibacterial agents of our invention include the 5-epi- analogs of 6'-alkylgentamicins B and C$_{1a}$ of 6'-N-alkyl-Antibiotic JI-20A, and of the compounds defined by formulae I and II wherein the 5-hydroxyl function has opposite stereochemistry to that in the compounds of formulae I and II, the 5-hydroxyl in the 5-epi- compound being axial while the 5-hydroxyl function in the compounds of formulae I and II are equatorial. Thus, compounds of this invention include 5-epiaminoglycosides such as:

6'-N-X-5-epi-gentamicin B,
6'-N-X-5-epi-gentamicin $C_{1a}$,
6'-N-X-5-epi-sisomicin,
6'-N-X-5-epi-Antibiotic JI-20A,
6'-N-X-5-epi-Antibiotic 66-40B, and
6'-N-X-5-epi-Antibiotic 66-40-D.

Other useful antibacterial agents of our invention are 6'-N-X-5-epi-W-4,6-di-O-(aminoglycosyl)-2,5-dideoxystreptamines including 6'-N-X-5-epi-W-5-deoxygentamicin B,
6'-N-X-5-epi-W-5-deoxygentamicin $C_{1a}$,
6'-N-X-5-epi-W-5-deoxysisomicin,
6'-N-X-5-epi-W-5-deoxy-Antibiotic JI-20A,
6'-N-X-5-epi-W-5-deoxy-Antibiotic 66-40B, and
6'-N-X-5-epi-W-5-deoxy-Antibiotic 66-40D, which compounds are defined by the following formulae III and IV:

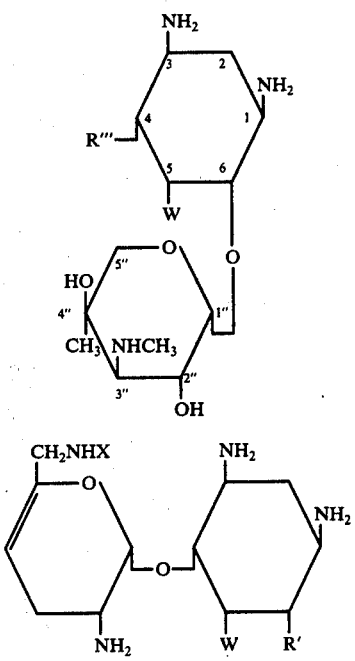

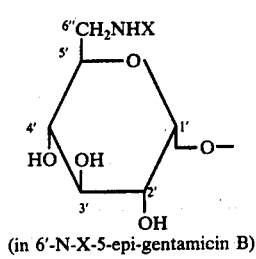

wherein W is amino or azido,
R' is as defined hereinabove for formula II;
and R''' includes R as defined for formula I and the following aminoglycosyl functions:

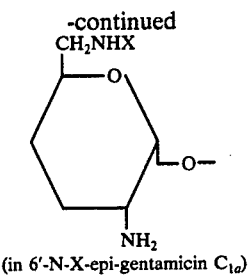
(in 6'-N-X-5-epi-gentamicin B)

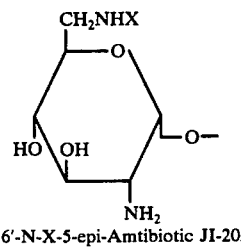
(in 6'-N-X-5-epi-gentamicin $C_{1a}$)

(in 6'-N-X-5-epi-Amtibiotic JI-20A)

Antibacterial agents defined by formula III thus include

6'-N-X-5-epi-amino-5-deoxygentamicin $C_{1a}$,
6'-N-X-5-epi-azido-5-deoxygentamicin $C_{1a}$,
6'-N-X-5-epi-amino-5-deoxygentamicin B,
6'-N-X-5-epi-azido-5-deoxygentamicin B,
6'-N-X-5-epi-amino-5-deoxysisomicin,
6'-N-X-5-epi-azido-5-deoxysisomicin,
6'-N-X-5-epi-amino-5-deoxy-Antibiotic JI-20A, and
6'-N-X-5-epi-azido-5-deoxy-Antibiotic JI-20A.

Compounds defined by formula IV are
6'-N-X-5-epi-amino-5-deoxy-Antibiotic 66-40B,
6'-N-X-5-epi-azido-5-deoxy-Antibiotic 66-40B,
6'-N-X-5-epi-amino-5-deoxy-Antibiotic 66-40D, and
6'-N-X-5-epi-azido-5-deoxy-Antibiotic 66-40D.

The 6'-N-X-Antibiotics Mu-1, 2, 4 and 5 of this invention include 6'-N-X-4-O-aminoglycosyl-6-O-garosaminyl-1,3-diaminocyclitols of the following formula V:

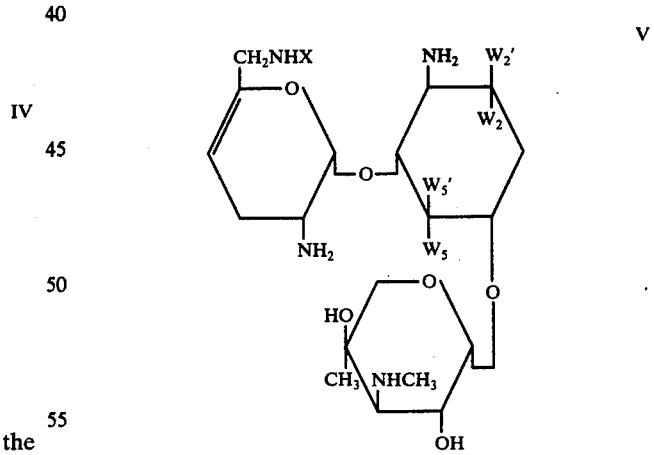

wherein X is as hereinabove defined, and in 6'-N-X-Antibiotic Mu-1, $W'_2$ and $W_5$ are hydrogen and $W_2$ and $W'_5$ are hydroxy;

in 6'-N-X-Antibiotic Mu-2, $W_2$, $W'_2$, $W_5$ and $W'_5$ are hydrogen;

in 6'-N-X-Antibiotic Mu-4, $W_2$ and $W_5$ are hydrogen and $W'_2$ and $W'_5$ are hydroxy; and in 6'-N-X-Antibiotic Mu-5, $W_2$, $W'_2$ and $W_5$ are hydrogen and $W'_5$ is amino.

The 6'-N-alkyl-4,6-di-O-(aminoglycosyl)-1,3-diaminocyclitols of this invention as defined by formulae I, II, III, IV and V are characterized by being white amorphous powders.

Also included within the composition-of-matter aspect of this invention are pharmaceutically acceptable acid addition salts of the 6'-N-X-4,6-di-O-(aminoglycosyl)-1,3-diaminocyclitols such as defined by formulae I – V which salts are made according to known procedures such as by neutralizing the free base with the appropriate acid, usually to about pH 5. Suitable acids for this purpose include acids such as hydrochloric, sulfuric, phosphoric, hydrobromic and the like. The physical embodiments of the acid addition salts of the 6'-N-X4,6-di-O-(aminoglycosyl)-1,3-diaminocyclitols are characterized by being white solids which are soluble in water and insoluble in most polar and non-polar organic solvents.

The 6'-N-X-4,6-di-O-(aminoglycosyl)-1,3-diaminocyclitols, such as defined by formulae I–V, particularly those of formulae I and II wherein the 1,3-diaminocyclitol is 2-deoxystreptamine (especially the 6-O-garosaminyl derivatives of formula I), and their non-toxic, pharmaceutically acceptable, acid addition salts, in general, exhibit broad spectrum antibacterial activity and possess a different spectrum compared to that of the parent antibiotics. Advantageously, the claimed compounds exhibit enhanced activity against organisms resistant to the parent compound. Thus, for example, compounds of this invention, e.g. the 6'-N-X-4-O-aminoglycosyl-6-O-garosaminyl2-deoxystreptamines, are more active against organisms which inactivate the parent antibiotics by acetylation of the 6'-amino group.

Particularly valuable compounds of this invention are 6'-N-X-4,6-di-O-(aminoglycosyl)-2-deoxystreptamines of formulae I and II, particularly the 6'-N-X derivatives (preferably 6'-N-ethyl) of sisomicin, Antibiotics 66-40B and 66-40D, which derivatives are broad spectrum antibacterial agents, being active against gram positive bacteria (e.g. *Staphylococcus aureus*) and gram negative bacteria (e.g. *Escherichia coli* and *Pseudomonas aeruginosa*) as determined by standard dilution tests, including bacteria resistant to the parent compounds, e.g. strains R5/W677 and HL97/W677 of E. coli and strain GN315 of *Pseudomonas aeruginosa*.

Other composition-of-matter aspects of this invention include N-protected derivatives of the 6'-N-X-4,6-di-O-(aminoglycosyl)-1,3-diaminocyclitols such as defined by formulae I-V wherein X is as defined hereinabove and wherein all protectable amino functions except the 6'-amino group are protected by groups susceptible to reductive cleavage (such as by treatment with hydrogen in the presence of a catalyst or by treatment with an alkali metal in liquid ammonia) or to basic or mild acid hydrolysis (such as with aqueous sodium hydroxide), which compounds are useful as intermediates in preparing the antibacterially active 6'-N-X-4,6-di-O-(aminoglycosyl)-1,3-diaminocyclitols of formulae I-V.

Useful amino protecting groups (designated by Z herein and in the claims) include hydrocarbon- carbonyl groups preferably having up to 8 carbon atoms, benzloxycarbonyl and tert.-butoxycarbonyl. Useful hydrocarboncarbonyl radicals are acyl radicals derived from lower alkanoic acids having up to 8 carbon atoms including acetyl, propionyl, n-butyryl, valeryl, and caprylyl, as well as acyl radicals derived from aralkanoic acids such as phenylacetyl and from arylcarboxylic acids such as o, m and p-toluoyl, mesitoyl, and benzoyl.

The foregoing amino protecting groups are removable by treatment with base (e.g. with sodium hydroxide) or, in the case of benzyloxycarbonyl, also by reductive cleavage methods known in the art, or, in the case of tert.-butoxycarbonyl, also by treatment with acid, e.g. trifluoroacetic acid.

Particularly useful intermediates of this group are 6'-N-X-4-O-aminoglycosyl-6-O-garosaminyl-1,3-diaminocyclitols of our invention wherein all amino groups except that at 6' are protected by acetyl, e.g. 1,3,2',3''-tetra-N-acetyl-6'-N-ethylsisomicin.

Another composition-of-matter aspect of this invention include intermediates which are per-N-protected derivatives of 4,6-di-O-(aminoglycosyl)-1,3-diaminocyclitols having a primary carbinamine at C-5' wherein the protecting group at the 6'-position (designated by Y herein and in the claims) is a member selected from the group consisting of trifluoroacetyl, benzyloxycarbonyl, and tert.-butoxycarbonyl, and wherein all other protecting groups, designated by Z herein and in the claims, are as hereinabove defined for Z in the above described 6'-N-X-poly-N-Z-4,6-di-O-(aminoglycosyl)-1,3-diaminocyclitol intermediates, with the proviso that in a given compound Y and Z are different, with Z being a group which remains intact under conditions in which Y is removed.

Of the 6'-N-Y-poly-N-Z-4,6-di-O-(aminoglycosyl)-1,3-diaminocyclitols of this composition-of-matter aspect of the invention, particularly useful as intermediates are those compounds wherein Y is tert.-butoxycarbonyl and Z is lower alkanoyl or benzyloxycarbonyl (e.g. 6'-N-tert.-butoxycarbonyl-1,3,2',3''tetra-N-acetylsisomicin and 6'-N-tert.-butoxycarbonyl-1,3,2',3''tetra-N-benzyloxycarbonylsisomicin) wherein the tert.-butoxycarbonyl group is easily removed by treatment with trifluoroacetic acid without affecting the alkanoyl or benzyloxycarbonyl groups.

Other useful intermediates of this composition-of-matter aspect are those wherein Y is benzyloxycarbonyl and Z is lower alkanoyl (e.g. 6'-N-benzyloxycarbonyl-1,3,2',3''-tetra-N-acetylsisomicin and 6'-N-benzyloxycarbonyl-1,3,2',3''-tetra-N-acetylgentamicin $C_{1a}$)- wherein the 6'-N-benzyloxycarbonyl group is easily removable by known reductive cleavage techniques (e.g. with sodium in ammonia in the case of the sisomicin derivative or hydrogen in the presence of palladium on charcoal in the case of the gentamicin derivative) without affecting the alkanoyl protecting groups, Z.

Still other intermediates of this group are those wherein Y is trifluoroacetyl and Z is tert.-butoxycarbonyl, benzyloxycarbonyl, or, preferably, lower alkanoyl (e.g. 6'-N-trifluoroacetyl-1,3,2',3''-tetra-N-tert.-butoxycarbonylsisomicin, 6'-N-trifluoroacetyl-1,3,2',3''-tetra-N-benzyloxycarbonylsisomicin, and 6'-N-trifluoroacetyl-1,3,2',3''-tetra-N-acetylsisomicin) wherein the 6'-N-trifluoroacetyl group is easily removed by treatment with a weak base, e.g. ammonium hydroxide, without removing the tert.-butoxycarbonyl, benzyloxycarbonyl or the lower alkanoyl amino protecting groups.

Preferred compounds of this composition-of-matter aspect are those wherein Y is trifluoroacetyl and Z is acetyl, including
6'-N-trifluoroacetyl-1,3,2',3''-tetra-N-acetylsisomicin,
6'-N-trifluoroacetyl-1,3,2',3''-tetra-N-acetylAntibiotic 66-40B, and
6'-N-trifluoroacetyl-1,3,2',3''-tetra-N-acetylAntibiotic 66-40D.

Other composition-of-matter aspects of this invention are 6'-N-unsubstituted-4,6-di-O-(aminoglycosyl)-1,3-diaminocyclitols wherein all amino functions other than the 6'-amino group are protected by protecting groups designated as Z wherein Z is as defined hereinabove. Thus, these compounds are compounds of formulae I-V wherein X is hydrogen and all amino functions other than the 6'-amino group are substituted by the group Z. These compounds are derived from the 6'-N-Y-poly-N-Z-4,6-di-O(aminoglycosyl)-1,3-diaminocyclitol described hereinabove by removal of the Y group as indicated above. Preferred compounds of this group are those wherein Z is lower alkanoyl, preferably acetyl.

The 6'-N-Y-per-N-Z-4,6-di-O-(aminoglycosyl)-1,3-diaminocyclitols, the 6'-N-unsubstituted-per-N-Z-4,6-di-O(aminoglycosyl)-1,3-diaminocyclitols and the 6'-N-X-per-N-Z-4,6-di-O-(aminoglycosyl)-1,3-diaminocyclitols described hereinabove are characterized by being white solids and are useful as intermediates in the process aspects of this invention described hereinbelow and in the Preparations and Examples.

GENERAL DESCRIPTION OF THE PROCESS ASPECTS OF THE INVENTION

In one process of this invention, a 6'-N-X derivative of an antibacterially active 4,6-di-O-(aminoglycosyl)-1,3-diaminocyclitol having a primary carbinamine at C-5' wherein X is as hereinabove defined for formulae I-V, is prepared by the reaction in an inert solvent of the corresponding 4,6-di-O-(aminoglycosyl)-1,3-diaminocyclitol having a primary carbinamine at C-5' and having all amino functions other than at position 6' protected by hydrocarboncarbonyl having up to 8 carbon atoms, benzyloxycarbonyl, or tert.-butoxycarbonyl groups, with at least one molar equivalent of a ketone or aldehyde, said ketone having the formula

wherein R and R' are each a lower alkyl having up to six carbon atoms, with the proviso that R and R' together have up to 7 carbon atoms, and said aldehyde having the formula R"CHO wherein R" is a substituent selected from the group consisting of alkyl, cycloalkyl, alkenyl, hydroxyalkyl, aminoalkyl, alkylaminoalkyl, cycloalkylalkyl, aminohydroxyalkyl, and alkylaminohydroxyalkyl, said substituent having up to 7 carbon atoms and, when said substituent is substituted by both hydroxyl and amino functions, only one of said functions can be attached to any one carbon atom; and when said substituent is substituted by an amino function, said amino function is protected by a hydrocarboncarbonyl, a benzyloxycarbonyl, or a tert.-butoxycarbonyl group;

followed by the reaction in situ of the 6'-N-substituted intermediate thereby formed with at least one equivalent of a hydride-donor reducing agent selected from the group consisting of a dialkylaminoborane, tetraalkylammonium cyanoborohydride, alkali metal cyanoborohydride, and alkali metal borohydride;

followed by removal of said amino function protecting groups by the reaction with aqueous base of the thereby formed 6'-N-X-4,6-di-O-(aminoglycosyl)-1,3-diaminocyclitol having hydrocarboncarbonyl, benzyloxycarbonyl, or tert.-butoxycarbonyl protecting groups; or, when said protecting groups are benzyloxycarbonyl, by reaction with an alkali metal in liquid ammonia; or, when said 6'-N-X-4,6-di-O-(aminoglycosyl)-1,3-diaminocyclitol having benzyloxycarbonyl protecting groups is devoid of unsaturation, by reaction with hydrogen in the presence of a catalyst; or, when said protecting groups are tert.-butoxycarbonyl, by reaction with aqueous acid.

This process, whereby the 6'-amino function in a 6'-N-unsubstituted-4,6-di-O-(aminoglycosyl)-1,3-diaminocyclitol antibacterial agent having a primary carbinamine at C-5' and all other amino functions protected by hydrocarboncarbonyl having up to 8 carbon atoms, benzyloxycarbonyl or tert.-butoxycarbonyl groups, is condensed with an aldehyde or a ketone and concommitantly reduced in situ in form a 6'-N-alkyl-4,6-di-O-(aminoglycosyl)-1,3-diaminocyclitol antibacterial agent, is usually carried out at room temperature in the presence of air, although it may be advantageously carried out under an inert atmosphere (e.g. argon or nitrogen). Advantageously, the reaction is completed within a short time, usually in a few hours, as determined by thin layer chromatography.

Hydride-donor reducing agents useful in our process include dialkylaminoboranes (e.g. dimethylaminoborane, diethylaminoborane and preferably morpholinoborane), tetraalkylammonium cyanoborohydride (e.g. tetrabutylammonium cyanoborohydride), alkali metal cyanoborohydride (e.g. lithium cyanoborohydride and sodium cyanoborohydride) and, preferably, alkali metal borohydride (e.g. sodium borohydride).

Our process is conveniently carried out at ambient temperatures in an inert solvent. By "inert solvent" is meant any organic or inorganic solvent in which the 4,6-di-O-(aminoglycosyl)-1,3-diaminocyclitol starting compounds and the reagents are soluble, and which will not interfere with the process under the reaction conditions thereof so there are produced a minimum of competing side reactions. Although anhydrous aprotic solvents may be sometimes advantageously employed in our process (such as tetrahydrofuran when utilizing morpholinoborane as hydride donor reducing agent) we usually carry out our process in protic solvents, e.g. in a lower alkanol or, preferably in water or in an aqueous lower alkanol (e.g. aqueous methanol, aqueous ethanol). Other water-miscible co-solvent systems may also be employed such as aqueous dimethylformamide, aqueous hexamethylphosphoramide, aqueous tetrahydrofuran and aqueous ethylene glycol dimethyl ether.

Typical ketones of the formula

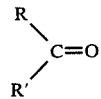

wherein R and R' are as above defined, which are useful in our process, include diethyl ketone, methyl ethyl ketone and, preferably, acetone.

Typical aldehydes of the formula R"CHO wherein R" is as above defined which are useful in our process include straight and branched chain alkyl aldehydes such as formaldehyde, acetaldehyde n-propanal, n-butanal, 2-methylpropanal, n-pentanal, 2-methylbutanal, 3-methylbutanal, 2,2-dimethylpropanal, n-hexenal, 2-ethylbutanal, n-heptanal and n-octanal; alkenyl aldehydes such as propenal, 2-methylpropenal, 2-butenal, 2-methyl-2-butenal, 2-ethyl-2-hexenal; hydroxy substituted straight and branched and chain alkyl aldehydes such as 5-hydroxypentanal, 2-hydroxy-3-methylbutanal, 2-hydroxy-2-methylpropanal, 4-hydroxybutanal, 2-hydroxypropanal and 8-hydroxyoctanal; N-protected amino substituted straight and branched chain alkyl aldehydes such as N-protected derivatives of 5-aminopentanal, 2-aminopropanal, 3-aminopropanal, 4-aminobutanal, 2-amino-3-methylbutanal, 8-aminooctanal and mono-N-alkyl derivatives thereof; and N-protected amino and hydroxy disubstituted straight and branched chain alkyl aldehydes such as N-protected derivatives of 2-hydroxy-5-aminopentanal, 3-hydroxy-3-methyl-4-aminobutanal, 2-hydroxy-4-aminobutanal, 2-hydroxy-3-aminopropanal, 2-hydroxy-2-methyl-3-aminopropanal, 2-amino-3-hydroxyoctanal, and mono-N-alkyl derivatives thereof.

In this process, if the aldehyde possesses a chiral center, one can use each enantiomer separately or together as a racemate and there will be obtained the respective diastereoisomers or a mixture thereof, respectively.

The aldehyde reagents useful in our process are either known compounds or are easily prepared from known compounds utilizing procedures well known in the art. Thus, for example, alkylaldehydes substituted by both hydroxyl and amino functions (e.g. 2-hydroxy-5-aminopentanal) may be prepared from an aminoaldehyde acetal (e.g. 4-aminobutanal diethylacetal) by protecting the amino function therein as an acetamido or phthalimido group utilizing known procedures followed by removal of the acetal function by acid hydrolysis thereby obtaining an N-protected aminoaldehyde (e.g. by converting 4-aminobutanal diethylacetal to the corresponding N-phthalimido derivative which upon acid hydrolysis yields 4-phthalimidobutanal). Treatment of the N-protected aminoaldehyde with hydrocyanic acid yields the corresponding N-protected-aminoalkyl hydroxynitrile (e.g. 2-hydroxy-5-phthalimidovaleronitrile) which upon catalytic reduction (e.g. hydrogen in the presence of palladium) or by hydride reduction (e.g. with di-isobutylaluminum hydride) yields an N-protected amino-hydroxy aldehyde (e.g. 2-hydroxy-5-phthalimido-pentanal) which is an aldehyde reagent used in our process.

When carrying out our process whereby a poly-N-protected derivative of a 6'-N-unsubstituted-4,6-di-O-(aminoglycosyl)-1,3-diaminocyclitol is treated with a hydride donor and an aldehyde, whereby is formed the corresponding poly-N-protected-6'-N-alkyl-4,6-di-O-(aminoglycosyl)-1,3-diaminocyclitol, to minimize competing side reactions when an aminoaldehyde is used as reagent, the amino function in the aldehyde ought be protected, e.g. with an acyl blocking group such as acetamido, phthalimido, or the like, prior to carrying out our process; thence, the N-protecting groups in the 6'-N-(protected aminoalkyl)-poly-N-protected-4,6-di-O-(aminoglycosyl)-1,3-diaminocyclitol thereby produced are removed. It may also be advantageous to protect the hydroxyl group in hydroxyl-containing aldehydes when carrying out our process; however, it is generally not necessary.

A convenient method of carrying out our process comprises preparing a solution of a 6'-N-unsubstituted-poly-N-Z-4,6-di-O-(aminoglycosyl)-1,3-diaminocyclitol wherein Z is as hereinabove defined, e.g. 1,3,2',3''-tetra-N-acetylsisomicin, in a protic solvent (preferably aqueous methanol), then adding at least a molar equivalent, and preferably a large molar excess of the desired alkyl aldehyde (e.g. acetaldehyde) followed within a short time (usually in about 5 minutes) by the addition of about a molar equivalent (based upon the starting poly-N-Z-4,6-di-O-(aminoglycosyl)-1,3-diaminocyclitol) of a hydride donor reducing reagent, preferably an alkali metal borohydride, usually sodium borohydride. The reaction is frequently completed in a few hours (e.g. three hours) as determined by thin layer chromatography and there is obtained the corresponding 6'-N-alkyl-poly-N-Z-4,6-di-O-(aminoglycosyl)-1,3-diaminocyclitol (e.g. 6'-N-ethyl-1,3,2',3''-tetra-N-acetylsisomicin). The protecting groups, Z, are then removed by treatment with aqueous base at elevated temperatures under an inert atmosphere, for example, by treatment with aqueous sodium hydroxide at 100° C under nitrogen. Alternatively, when the protecting groups, Z, are tert.-butoxycarbonyl, removal thereof is effected by treatment with acid, e.g. trifluoroacetic acid. Alternatively, when the protecting groups, Z, are benzyloxycarbonyl, they are conveniently removed via reductive techniques, sodium in liquid ammonia being preferred for aminoglycoside derivatives having double bonds (e.g. 1,3,2',3''-tetra-N-benzyloxycarbonylsisomicin), and hydrogenation of the presence of palladium on charcoal catalyst being preferred for saturated aminoglycosides (e.g. 1,3,2',3''-tetra-N-benzyloxycarbonylgentamicin $C_{1a}$). Isolation and purification of the 6'-N-alkyl derivative thereby produced is then effected utilizing known techniques such as precipitation, extraction and, preferably, chromatographic techniques.

Our process thus provides a convenient, one-vessel process whereby a per-N-protected-6'-N-unsubstituted aminoglycoside is reacted in situ with an aldehyde (preferably in excess quantities) and with a hydride-donor reducing agent to produce a 6'-N-alkylated derivative (e.g. 6'-N-ethylsisomicin).

ANOTHER PROCESS ASPECT OF THE INVENTION

The 6'-N-uprotected-per-N-Z-4,6-di-O-(aminoglycosyl)-1,3-diaminocyclitols having a primary carbinamine at C-5' wherein Z is a hydrocarboncarbonyl having up to 8 carbon atoms, benzyloxycarbonyl, or tert.-butoxycarbonyl group, requisite intermediates for the above described process of this invention, are prepared via another process of the invention by the reaction of an unprotected 4,6-di-O-(aminoglycosyl)-1,3-diaminocyclitol having a primary carbinamine at C-5' with about one molar equivalent of an acylating reagent selected from the group consisting of ethyl trifluorothiolacetate, tert.-butoxycarbonyl azide, trifluoroacetylimidazole, and N-[benzyloxycarbonyloxy]-succinimide;

followed by the reaction of the 6'-N-acyl derivative thereby formed, said acyl being a member selected from the group consisting of trifluoroacetyl, tert.-butoxycarbonyl, and benzyloxycarbonyl, with a second acylating agent having a substituted carbonyl radical (Z) selected from the group consisting of a hydrocarboncarbonyl halide having up to 8 carbon atoms, a hydrocarboncarboxylic acid anhydride wherein said hydrocarbon has up to 7 carbon atoms, tert.-butoxycarbonyl azide, benzyloxycarbonyl halide and N-[benzyloxycarbonyloxy]-succinimide, the molar quantity of said second acylating agent being at least equivalent to the molar quantity of said 4,6-di-O-(aminoglycosyl)-1,3-diaminocyclitol multiplied by the number of amino functions therein excluding the 6'-amino function, with the proviso that said substituted carbonyl radical Z in said second acylating agent is one which, when substituted on a nitrogen atom, will remain intact under conditions which will remove said 6'-N-acyl;

followed by the reaction of the thereby formed 6'-N-acyl-per-N-Z-4,6-di-O-(aminoglycosyl)-1,3-diaminocyclitol wherein Z is a member selected from the group consisting of hydrocarboncarbonyl having up to 8 carbon atoms, tert.-butoxycarbonyl and benzyloxycarbonyl, Z being different from said 6'-N-acyl and being a group which remains intact under conditions which will remove said 6'-N-acyl, with a weak base when said 6'-N-acyl is 6'-N-trifluoroacetyl, or reaction with trifluoroacetic acid when said 6'-N-acyl is 6'-N-tert.-butoxycarbonyl, or when said 6'-N-acyl is benzyloxycarbonyl, by reaction with an alkali metal in liquid ammonia or when said 4,6-di-O-(aminoglycosyl)-2-deoxystreptamine is devoid of unsaturations, by reaction with hydrogen in the presence of palladium on charcoal.

Typical 4,6-di-O-(aminoglycosyl)-1,3-diaminocyclitol antibacterial precursors for the 6-unsubstituted-per-N-Z-substituted compounds of our invention include Antibiotics 66-40B and 66-40D and 4-O-aminoglycosyl-6-O-garosaminyl-2-deoxystreptamine antibiotics having a primary carbinamine at C-5' (i.e. the grouping "-CH$_2$NH$_2$" at C-5') such as sisomicin, related 4,6-di-O-(aminoglycosyl)-1,3-diaminocyclitols such as the 5-epi-, the 5-epi-azido-5-deoxy-, and the 5-epi-amino-5-deoxy- analogs of the foregoing and of gentamicins B and C$_{1a}$ and Antibiotic JI-20A, as well as related 4-O-aminoglycosyl-6-O-garosaminyl-1,3-diaminocyclitols such as Antibiotic Mu-1, Antibiotic Mu-2, Antibiotic Mu-4 and Antibiotic Mu-5. Of the foregoing, preferred starting antibiotic precursors are Antibiotic 66-40B, Antibiotic 66-40D, and particularly sisomicin, all of which lead to preferred compounds of this invention, i.e. to the corresponding 6'-N-alkyl derivatives.

Most of the aforementioned 4,6-di-O-(aminoglycosyl)-1,3-diaminocyclitol antibiotics are known. The 5-epi- analogs of sisomicin, of gentamicins B and C$_{1a}$, and of Antibiotics JI-20A, 66-40B and 66-40D, their preparation and properties are described in the co-pending application of Peter J. L. Daniels for 5-EPI-4,6-DI-O-(AMINOGLYCOSYL)-2-DEOXYSTREPTAMINES, METHODS FOR THEIR MANUFACTURE AND INTERMEDIATES USEFUL THEREIN, METHODS FOR THEIR USE AN ANTIBACTERIAL AGENTS AND COMPOSITIONS USEFUL THEREFOR, U.S. Ser. No. 528,593 filed Nov. 29, 1974; the 5-epi-azido-5-deoxy- and 5-epi-amino-5-deoxy- analogs of sisomicin, gentamicins B and C$_{1a}$ and of Antibiotics JI-20A, 66-40B and 66-40D are described in co-pending application of Peter J. L. Daniels for 5-EPI-AZIDO-4,6-DI-O-(AMINOGLYCOSYL)-2,5-DIDEOXYSTREPTAMINES, METHODS FOR THEIR MANUFACTURE AND INTERMEDIATES USEFUL THEREIN, METHODS FOR THEIR USE AS ANTIBACTERIAL AGENTS AND COMPOSITIONS USEFUL THEREFOR, U.S. Ser. No. 528,592 filed Nov. 29, 1974, now abandoned; while Antibiobics Mu-1, 2, 4 and 5, their preparation, isolation, properties and planar configuration, are described in co-pending application of Marvin J. Weinstein, Peter J. L. Daniels, Gerald H. Wagman, and Raymond Testa for MUTAMICINS AND METHODS FOR THE PREPARATION THEREOF, U.S. Ser. No. 443,052 filed Feb. 15, 1974, now abandoned, of common assignee as the instant application. In this application, the antibiotics are named therein as mutamicin 1, mutamicin 2, mutamicin 4 and mutamicin 5, but are the same 4-O-aminoglycosyl-6-O-garosaminyl-1,3-diaminocyclitol antibiotics starting compounds identified herein as Antibiotics Mu-1, Mu-2, Mu-4 and Mu-5, respectively, being compounds of formula III wherein X is hydrogen.

In the first step of this process, an unprotected-4,6-di-O-(aminoglycosyl)-1,3-diaminocyclitol having a primary carbinamine at C-5' (e.g. sisomicin) is treated with about one molar equivalent of an acylating agent selected from the group consisting of ethyl trifluorothiolacetate, trifluoroacetylimidazole, tert.-butoxycarbonyl azide and N-[benzyloxycarbonyloxy]succinimide, usually in a lower alkanol, whereby the amino group at C-6' is selectively N-acylated and there is produced the corresponding 6'-N-trifluoroacetyl derivative (in the case of the first two acylating agents) or 6'-N-tert.-butoxycarbonyl derivative or the 6'-N-benzyloxycarbonyl derivative. Isolation and purification of the resulting 6'-N-acyl-4,6-di-O-(aminoglycosyl)-1,3-diaminocyclitol thereby produced is effected via techniques known in the art, usually via chromatographic techniques.

In carrying out this step of the process with an aminoglycoside starting compound having a double bond, such as is present in sisomicin, 6'-N-trifluoroacetyl derivative is preferable. In general, when preparing 6'-N-acyl intermediates, the preferred reagent for unsaturated aminoglycosides is ethyl trifluorothiolacetate whereby are prepared 6'-N-trifluoroacetyl-4,6-di-O-(aminoglycosyl)-1,3-diaminocyclitols of this invention.

In the second step of this process aspect of the invention, the 6'-N-acyl derivative (i.e. 6'-N-Y), prepared as described above, is treated (usually in a lower alkanol as solvent) with a second acylating reagent having a substituted carbonyl radical (Z), the molar quantity of which is at least equivalent to, and preferably is in excess of, the number of amino groups present in the aminoglycoside molecule excluding the 6'-amino function, said reagent being either a hydrocarboncarbonyl halide having up to 8 carbon atoms or a hydrocarboncarboxylic acid anhydride wherein said hydrocarbon has up to 7 carbon atoms whereby are prepared a 6'-N-Y-poly-N-hydrocarbonacarbonyl derivative having up to 8 carbon atoms; or a tert.-butoxycarbonyl azide, whereby is prepared a 6'-N-Y-poly-N-tert.-butoxycarbonyl derivative, a benzyloxycarbonyl halide or an N-[benzyloxycarbonyloxy]succinimide whereby is pepared a 6'-N-Y-poly-N-benzyloxycarbonyl derivative, with the proviso that the substituted carbonyl radical Z in said second acylating agent is one which, when substituted on a nitrogen atom, will remain intact under conditions which will remove said acyl radical (Y) of said 6'-N-acyl (i.e. 6'-N-Y) derivative.

Thus, as disclosed hereinabove in the discussion of the 6'-N-Y-per-N-Z-4,6-di-O-(aminoglycosyl)-1,3-diaminocyclitol compounds of the invention, when the 6'-N-acyl group is tert.-butoxycarbonyl, the second acylating reagent must be other than tert.-butoxycarbonyl azide; when the 6'-N-acyl group is benzyloxycarbonyl, the second acylating reagent must be other than benzyloxycarbonyl halide or N-[benzyloxycarbonyloxy] succinimide; and when the 6'-N-acyl groupis trifluoroacetyl, the second acylating reagent may be any of the reagents listed hereinabove.

The preferred reagent of this step of the process is a lower alkanoyl anhydride in a lower alkanol, particularly acetic anhydride in methanol, and preferred starting compounds are those wherein the 6'-N-acyl function is a 6'-N-trifluoro- acetyl-per-N-acetyl-4-O-aminoglycosyl-6-O-garosaminyl-1,3- diaminocyclitols, preferred intermediates of this process.

In the last step of this process whereby 6'-unsubstituted-poly-N-Z-4,6-di-O-(aminoglycosyl)-1,3-diaminocyclitol (requisite intermediates for the first process aspect of this invention) are prepared, the 6'-N-Y-poly-N-Z-4,6-di-O- (aminoglycosyl)-1,3-diaminocyclitols, prepared as described hereinabove, are subjected to conditions which will remove the 6'-N-Y function without cleaving the poly-N-Z functions, said conditions having been disclosed hereinabove and in the preparations.

In a preferred mode of carrying out this process aspect of the invention, a 4,6-di-O-(aminoglycosyl)- 1,3-diaminocyclitol, having a primary carbinamine at C-5'(e.g. sisomicin) is reacted with about a molar equivalent of ethyl trifluorothiolacetate in aqueous methanol followed by the reaction of the thereby formed 6'-N-trifluoroacetyl (i.e. 6'-N-Y) derivative (e.g. 6'-N-trifluoroacetylsisomicin) with an alkanoic anhydride (e.g. acetic anhydride) in methanol; and thence cleavage of the 6'-N-Y group in the resulting 6'-N-Y-poly-N-Z derivative, i.e. cleavage of the 6'-N-trifluoracetyl group in the resulting 6'-N-trifluoroacetyl-poly-N-acetyl-4,6-di-O- (aminoglycosyl)-1,3-diaminocyclitols (e.g. 6'-N-trifluoroacetyl- 1,3,2',3''-tetra-N-acetylsisomicin) by treatment with mild base (e.g. ammonium hydroxide) and isolation of the 6'-N-unsubstituted-per-N-Z-aminoglycoside thereby formed (i.e. 1,3,2',3''-tetra-N- acetylsisomicin).

It is apparent from the foregoing that by out invention known 4,6-di-O-(aminoglycosyl)-1,3-diaminocyclitol antibiotics are converted to the corresponding 6'-unsubstituted-poly-N-substituted aminoglycoside, which, upon treatment with an aldehyde or ketone followed by the reaction in situ of the resulting 6'-N-substituted derivative with a hydride-donor reducing agent, yields 6'-N-alkyl-4,6-di-O-(aminoglycosyl)-1,3-diaminocyclitols, possessing antibacterial activity.

The processes described hereinabove are illustrated in detail hereinbelow in the Preparations and Examples which, however, should not be construed as limiting the scope of our invention.

PREPARATION OF INTERMEDIATES

PREPARATION 1—6'-N-UNSUBSTITUTED-POLY-N-ACETYLAMINOGLYCOSIDES

A. 6'-N-Trifluoroacetylaminoglycosides (1) 6'-N-trifluoroacetylsisomicin

Dissolve 45 gms. of sisomicin (100.6 mmoles) in 1100 ml. of methanol, slowly add over a period of 10–30 minutes with stirring a solution of 13.5 ml. of ethyltrifluorothiolacetate (105 mmoles, 1.05 equivalents) in 75 ml. of methanol. Stir the solution at room termperature for an additional period of ½ to 2 hours, then evaporate in vacuo to a residue comprising 6'-N-trifluoroacetylsisomicin, which is used without further purification in following Preparation 1B (1).

2. In a manner similar to that described in Preparation 1A(1) treat each of the following aminoglycosides with ethyltrifluoro-thiolacetate in methanol:
a. Gentamicin $C_{1a}$,
b. Gentamicin B,
c. Antibiotic JI-20A,
d. Antibiotic 66-40B,
e. Antibiotic 66-40D,
f. the 5-epi-, 5-epi-amino-5-deoxy-, and the 5-epi-azido-5-deoxy- analogs of the foregoing,
g. Antibiotic Mu-1,
h. Antibiotic Mu-2,
i. Antibiotic Mu-4, and
j. Antibiotic Mu-5.

Isolate each of the resulting products in a manner similar to that described hereinabove to obtain, respectively,
a. 6'-N-trifluoroacetylgentamicin $C_{1a}$,
b. 6'-N-trifluoroacetylgentamicin B,
c. 6'-N-trifluoroacetyl-Antibiotic JI-20A,
d. 6'-N-trifluoroacetyl-Antibiotic 66-40B,
e. 6'-N-trifluoroacetyl-Antibiotic 66-40D,
f. the 5-epi-, 5-epi-amino-5-deoxy-, and the 5-epi-azido-5-deoxy- analogs of the foregoing,
g. 6'-N-trifluoroacetyl-Antibiotic Mu-1,
h. 6'-N-trifluoroacetyl-Antibiotic Mu-2,
i. 6'-N-trifluoroacetyl-Antibiotic Mu-4, and
j. 6'-N-trifluoroacetyl-Antibiotic Mu-5.

B. 6'-Trifluoroacetyl-Poly-N-Acetylaminoglycosides (1) 1,3,2',3''-tetra-N-acetyl-6'-N-trifluoroacetylsisomicin Dissolve 6'-N-trifluoroacetylsisomicin prepared as described in Preparation 1A(1) in 900 ml. of methanol. Cool the solution to about -4° C, then add with stirring 67.5 ml. of acetic anhydride (715 mmoles, 7.05 equivalents). Stir the solution at room temperature for a period of from about 2 to 18 hours until the reaction is complete as determined by thin layer chromatography. Evaporate the solution in vacuo to a residue comprising 1,3,2',3'' -tetra-N-acetyl-6'-N-trifluoroacetylsisomicin.

2. In a manner similar to that described in Preparation 1B(1) treat each of the products obtained in Preparation 1A(2) with acetic anhydride in methanol. Isolate and purify each of the resultant products in a manner similar to that described to obtain, respectively,
a. 1,3,2',3''-tetra-N-acetyl-6'-N-trifluoroacetylgentamicin $C_{1a}$,
b. 1,3,3''-tri-N-acetyl-6'-N-trifluoroacetylgentamicin B,
c. 1,3,2',3''-tetra-N-acetyl-6'-N-trifluoroacetyl-Antibiotic JI-20A,
d. 1,3,2',3''-tetra-N-acetyl-6'-N-trifluoroacetyl-Antibiotic 66-40B,
e. 1,3,2',3''-tetra-N-acetyl-6'-N-trifluoroacetyl-Antibiotic 66-40D,
f. the 5-epi-, 5-epi-N-acetylamino-5-deoxy- and 5-epi-azido-5-deoxy- analogs of the foregoing,
g. 1,3,2',3''-tetra-N-acetyl-6'-N-trifluoroacetyl-Antibiotic Mu-1,
h. 1,3,2',3''-tetra-N-acetyl-6'-N-trifluoroacetyl-Antibiotic Mu-2,
i. 1,3,2',3''-tetra-N-acetyl-6'-N-trifluoroacetyl-Antibiotic Mu-4, and
j. 1,3,5,2',3''-penta-N-acetyl-6'-N-trifluoroacetyl-Antibiotic Mu-5, C. 6'-N-Unsubstituted-Poly-N-Acetylaminoglycosides (1) 1,3,2',3''-tetra-N-acetylsisomicin Dissolve the 1,3,2',3''-tetra-N-acetyl-6'-N-trifluoroacetylsisomicin prepared as described in Preparation 1B (1) in methanol. Add 500 ml. of 28% aqueous ammonium hydroxide and allow the solution to stand at room temperature overnight. Evaporate the solution in vacuo to a residue comprising 1,3,2',3''-tetra-N-acetylsisomicin. Purify by chromatographing on silica gel eluting with a solvent mixture comprising chloroform:methanol:14% ammonium hydroxide (27.7:6:1), taking 20 ml. fractions. Monitor the eluted fractions via thin layer chromatography on silica gel using the lower phase of chloroform: methanol:28% ammonium hydroxide (1:1:1) as developer. Combine like fractions and evaporate in vacuo to a residue of 1,3,2',3''-tetra-N-acetylsisomicin having the following physical constants: $[\alpha]_D^{26} + 207.4°$ (c, 0.3, H$_2$0); characteristic mass spectral peaks at m/e 615 (M.+), 598, 443, 425, 415, 397, 275, 257, 247, 229, 202, 169; pmr peaks (60 MHz, D$_2$O) at δ1.07, 1.17 (3H, C-Me rotamers), 1.95, 1.98, 2.03 (12H, NCOMe), 3.13, 3.00 (3H, N-Me rotamers), 5.29 (1H, d, J=4Hz, H-1''), 5.64 (1H, d, J=2.5Hz, H-1')ppm.

2. In a manner similar to that described in Preparation 1C(1) treat each of the 6'-N-trifluoroacetyl-poly-N-acetylaminoglycosides of Preparation 1B(2) with aqueous ammonium hydroxide. Isolate and purify each of the resultant products in a manner similar to that described to obtain, respectively, a. 1,3,2',3''-tetra-N-acetylgentamicin C$_{1a}$,
b. 1,3,3''-tri-N-acetylgentamicin B,
c. 1,3,2',3''-tetra-N-acetyl-Antibiotic JI-20A,
d. 1,3,2',3''-tetra-N-acetyl-Antibiotic 66-40B,
e. 1,3,2',3''-tetra-N-acetyl-Antibiotic 66-40D,
f. the 5-epi-, 5-epi-N-acetylamin-5-deoxy-, and 5-epi-azido-5-deoxy- analogs of the foregoing,
g. 1,3,2',3''-tetra-N-acetyl-Antibiotic Mu-1,
h. 1,3,2',3''-tetra-N-acetyl-Antibiotic Mu-2,
1. i. 1,3,2',3''-tetra-N-acetyl-Antibiotic Mu-4, and
j. 1,3,5,2',3''-penta-N-acetyl-Antibiotic Mu-5.

PREPARATION 2—6'-N-UNSUBSTITUDED-POLY-N-ACETYLAMINOGLYCOSIDES VIA THE 6'-N-t-BUTOXYCARBONYL INTERMEDIATE

A. 6'-N-t-butoxycarbonylaminoglycosides (1) 6'-N-t-butoxycarbonylgentamicin C$_{1a}$ To a stirred solution of gentamicin C$_{1a}$ (2.69 gms., 6 mmoles) in 50% aqueous methanol containing triethylamine (1.82 ml.), cooled to 5° C and t-butoxycarbonyl azide (1.91 gms., 13.4 mmoles). Stir the reaction mixture for 18 hours at 5° C, then add Amberlite IRA-401S ion exchange resin (OH$^-$ cycle) and continue stirring for an additional 30 minutes. Remove the resin by filtration, concentrate the filtrate in vacuo, chromatograph the resultant residue over silica gel using the lower phase of a 2:1:1, chloroform:methanol:concentrated ammonium hydroxide solvent system. Monitor the fractions by thin layer chromatography and combine those containing the pure major product and lyophilize to a residueof 6'-N-t-butoxycarbonylgentamicin C$_{1a}$ (0.42 gms., 13%), $[\alpha]_D^{26}$ + 137° (c, 0.3, MeOH); pmr δ 1.23 (3H, s, C-CH$_3$), 1.45 (9H, s, C(CH$_3$)$_3$), 2.53 (3H, s, N-CH$_3$), 5.08 ppm (2H, overlapping doublets, J≃3.5Hz); mass spectrum m/e 550 (MH)+, 549 M+, 419, 401, 391, 373 (6'-N-t-butoxcarbonylgentamine C$_{1a}$), 350, 332, 322, 304 (garosamine-2-deoxystreptamine), 191, 173, 163, 145 (2-deoxystreptamine), 229 (6'-N-t-butoxycarbonylpurpurosamine C), 160 (garosamine).

2. In a manner similar to that described in above Preparation 2A(1) treat each of the following aminoglycosides with t-butoxycarbonyl azide in aqueous methanol and triethylamine.

a. Gentamicin B,
b. Antibiotic JI-20A,
c. Antibiotic 66-40B,
d. Antibiotic 66-40D, and
e. the 5-epi-, 5-epi-amino-5-deoxy- and 5-epi-azido-5-deoxy- analogs of the foregoing. Isolate and purify each of the resultant products in a manner similar to that described in Example 2A(1) to obtain, respectively, a. 6'-N-t-butoxycarbonylgentamicin B,
b. 6'-N-t-butoxycarbonly-Antibiotic JI-20A,
c. 6'-N-t-butoxycarbonyl-Antibiotic 66-40B,
d. 6'-N-t-butoxycarbonyl-Antibiotic 66-40D, and
e. the 5-epi-, 5-epi-amino-5-deoxy-, and 5-epi-azido-5-deoxy- analogs of the foregoing.

B. 6'-N-t-butoxycarbonyl-poly-N-alkanoylaminoglycosides

In a manner similar to that described in Preparation 1B (1) treat each of the 6'-N-t-butoxycarbonylaminoglycosides prepared in Preparation 2A(1) and 2A(2) with acetic anhydride in methanol. Isolate and purify each of the resultant products in a manner similar to that described in Preparation 1B(1) to obtain, respectively, 1. 1,3,2',3''-tetra-N-acetyl-6'-N-t-butoxycarbonylgentamicin C$_{1a}$,
2. 1,3,3''-tri-N-acetyl-6'-N-t-butoxycarbonylgentamicin B,
3. 1,3,2',3''-tetra-N-acetyl-6'-N-t-butoxycarbonyl-Antibiotic JI-20A,
4. 1,3,2',3''-tetra-N-acetyl-6'-N-t-butoxycarbonyl-Antibiotic 66-40B,
5. 1,3,2',3''-tetra-N-acetyl-6'-N-t-butoxycarbonyl-Antibiotic 66-40D,
6. the 5-epi-, 5-epi-N-acetylamino-5-deoxy-, and 5-epi-azido-5-deoxy- analogs of the foregoing.

C. 6'-N-Unsubstituted-Poly-N-Acetylaminoglycosides (1) 1,3,2',3''-tetra-N-acetylgentamicin C$_{1a}$ Dissolve 1,3,2',3''-tetra-N-acetyl-6'-N-t-butoxycarbonylgentamicin C$_{1a}$ in trifluoroacetic acid and allow the solution to stand for 10 minutes. Pour the solution into ether and filter the resultant precipitate comprising 1,3,2',3''-tetra-N-acetylsisomicin trifluoroacetate. Dissolve the foregoing trifluoroacetic acid salt in water, pour onto an IRA-401S resin column in the OH$^-$ cycle, elute with water, combine the eluates and lyophilize to a residue comprising 1,3,2',3''-tetra-N- acetylgentamicin C$_{1a}$.

2. In a manner similar to that described in Preparation 2C(1) treat each of the following with trifluoroacetic acid.

a. 1,3,3''-tri-N-acetyl-6'-N-t-butoxycarbonylgentamicin B,
b. 1,3,2',3''-tetra-N-acetyl-6'-N-t-butoxycarbonyl-Antibiotic JI-20A,
c. 1,3,2',3''-tetra-N-acetyl-6'-N-t-butoxycarbonyl-Antibiotic 66-40B,
d. 1,3,2',3''-tetra-N-acetyl-6'-N-t-butoxycarbonyl-Antibiotic 66-40D,
e. the 5-epi-, 5-epi-N-acetylamino-5-deoxy-, and 5-epi-azido-5-deoxy- analogs of the foregoing.

Isolate and purify each of the resultant products in a manner similar to that described in Preparation 2C(1) to obtain, respectively, a. 1,3,3''-tri-N-acetylgentamicin B,
b. 1,3,2',3''-tetra-N-acetyl-Antibiotic JI-20A,
c. 1,3,2',3''-tetra-N-acetyl-Antibiotic 66-40B,
d. 1,3,2',3''-tetra-N-acetyl-Antibiotic 66-40D,
e. the 5epi-, 5-epi-N-acetylamino-5-deoxy-, and 5-epi-azido-5-deoxy- analogs of the foregoing.

3. In the procedure of Preparation 2B by substituting for acetic anhydride the anhydride of other lower alkanoic acids, e.g. propionic anhydride, valeric anhydride and caprylic anhydride, there is obtained the corresponding poly-N-lower alkanoyl-6'-N-t-butoxycarbonylaminoglycosides, i.e.

1a 1,3,2',3''-tetra-N-propionyl-6'-N-t-butoxycarbonylgentamicin $C_{1a}$,
1b. 1,3,2',3''-tetra-N-valeryl-6'-N-t-butoxycarbonylgentamicin $C_{1a}$,
1c. 1,3,2',3''-tetra-N-caprylyl-6'-N-t-butoxycarbonylgentamicin $C_{1a}$;
2a. 1,3,3''-tri-N-propionyl-6'-N-t-butoxycarbonylgentamicin B,
2b. 1,3,3''-tri-N-valeryl-6'-N-t-butoxycarbonylgentamicin B,
2c. 1,3,3''-tri-N-caprylyl-6'-N-t-butoxycarbonylgentamicin B;
3a. 1,3,2',3''-tetra-N-propionyl-6'-N-t-butoxycarbonyl-Antibiotic JI-20A,
3b. 1,3,2',3''-tetra-N-valeryl-6'-N-t-butoxycarbonyl-Antibiotic JI-20A,
3c. 1,3,2',3''-tetra-N-caprylyl-6'-N-t-butoxycarbonyl-Antibiotic JI-20A;
4a. 1,3,2',3''-tetra-N-propionyl-6'-N-t-butoxycarbonyl-Antibiotic 66-40B,
4b. 1,3,2',3''-tetra-N-valeryl-6'-N-t-butoxylcarbonyl-Antibiotic 66-40B,
4c. 1,3,2',3''-tetra-N-caprylyl-6'-N-t-butoxycarbonyl-Antibiotic 66-40B;
5a. 1,3,2',3''-tetra-N-propionyl-6'-N-t-butoxycarbonyl-Antibiotic 66-40D,
5b. 1,3,2',3''-tetra-N-valeryl-6'-N-t-butoxycarbonyl-Antibiotic 66-40D,
5c. 1,3,2',3''-tetra-N-caprylyl-6'-N-t-butoxycarbonyl-Antibiotic 66-40D;
6. the 5-epi-N-propionyl (or valeryl- or caprylyl)-amino-5-deoxy- and 5-epi-azido-5-deoxy-analogs of the foregoing.

3. In a manner similar to that described in Preparation 2C(1) treat each of the poly-N-lower alkanoyl-6'-N-tert.-butoxycarbonyl-aminoglycosides prepared in Preparation 2B with trifluoroacetic acid and isolate each of the resultant products to obtain, respectively, 1a. 1,3,2',3''-tetra-N-propionylgentamicin $C_{1a}$,
1b. 1,3,2',3''-tetra-N-valerylgentamicin $C_{1a}$,
1c. 1,3,2',3''-tetra-N-caprylylgentamicin $C_{1a}$;
2a. 1,3,3''-tri-N-propionylgentamicin B,
2b. 1,3,3''-tri-N-valerylgentamicin B,
2c. 1,3,3''-tri-N-caprylylgentamicin B;
3a. 1,3,2',3''-tetra-N-propionyl-Antibiotic JI-20A,
3b. 1,3,2',3''-tetra-N-valeryl-Antibiotic JI-20A,
3c. 1,3,2',3''-tetra-N-caprylyl-Antibiotic JI-20A;
4a. 1,3,2',3''-tetra-N-propionyl-Antibiotic 66-40B,
4b. 1,3,2',3''-tetra-N-valeryl-Antibiotic 66-40B,
4c. 1,3,2',3''-tetra-N-caprylyl-Antibiotic 66-40B;
5a. 1,3,2',3''-tetra-N-propionyl-Antibiotic 66-40D,
5b. 1,3,2',3''-tetra-N-valeryl-Antibiotic 66-40D,
5c. 1,3,2',3''-tetra-N-caprylyl-Antibiotic 66-40D;
6. the 5-epi-, 5-N-propionyl (or valeryl- or caprylyl)-amino-5-deoxy-, and 5-epi-azido-5-deoxy- analogs of the foregoing.

PREPARATION 3

PREPARATION OF ALDEHYDE INTERMEDIATES

A. 2-Acetamido-3-Hydroxyoctanal

Protect the amino function in the 2-amino-3-hydroxyoctanoic acid by conversion thereof to an acetamido function by reaction with acetic anhydride, then esterify the resultant 2-acetamido-3-hydroxyoctanoic acid with methanol; reduce the resultant 2-acetamido-3-hydroxyoctanoic acid methyl ester with diisobutylaluminum hydride according to known procedures to obtain 2-acetamido-3-hydroxyoctanal.

B. 4-Acetamidobutyraldehyde

Dissolve 5 gms. of 4-acetamidobutyraldehyde diethyl acetal in 75 ml. of distilled water and 5 ml. of 1 N sulfuric acid. Allow the solution to stand at room temperature until the hydrolysis is complete as determined by thin layer chromatography. Neutralize the solution with sodium bicarbonate, then saturate the solution with sodium chloride and extract with chloroform. Distill the combined chloroform extracts to a residue comprising 4-acetamidobutyraldehyde, which can be used without further purification in the procedure of Example 7A.

C. 2-Acetoxy-4-(N-Methylacetamido)Butanal

Treat the diethylacetal of 2-hydroxy-4-aminobutanal with acetic anhydride in pyridine followed by treatment of the resulting diethylacetal of 2-acetoxy-4-acetamidobutanal with sodium hydride and methyl iodide to obtain the diethylacetal of 2-acetoxy-4-(N-methylacetamido)butanal. Remove the acetal protecting group by means of acid to obtain 2-acetoxy-4-(N-methylacetamido)butanal.

EXAMPLE 1

6'-N-ETHYLAMINOGLYCOSIDES

A. 6'-N-Ethylsisomicin

1. Dissolve 5.25 gms. of 1,3,2', 3''-tetra-N-acetylsisomicin (8.5 mmoles) in 62 ml. of 90% methanol. While stirring the solution add 1.4 ml. of acetaldehyde (24.8 mmoles, 2.9 equivalents) and then slowly add 0.35 gms. of sodium borohydride (11 mmoles, 1.3 equivalents). Continue stirring the reaction mixture at room temperature for 3 hours, then evaporate to a residue. Dissolve the residue in a minimum of water and pass over a column (25 ml.) of IRA-401S (hydroxide form) resin. Elute with water, combine like eluates, and evaporate to a residue comprising 1,3,2',3''-tetra-N-acetyl-6'-N-ethylsisomicin.

2. Add 30 ml. of 1 N sodium hydroxide to the 1,3,2',3''-tetra-N-acetyl-6'-N-ethylsisomicin residue of Example 1A(1) and reflux overnight. Pass the solution over a 225 ml. column of IRC-50 (proton form) resin. Elute with 3% aqueous ammonium hydroxide, evaporate the combined ammonium hydroxide eluates and chromatograph the resultant residue on silica gel eluting with the lower phase of a solvent system comprising chloroform: methanol:ammonium hydroxide (15%) (2:1:1). Monitor the fractions by thin layer chromatography on silica gel plates eluting with the lower phase of chloroform:methanol:ammonium hydroxide (28%) (1:1:1) as solvent. Pool like fractions and evaporate in vacuo to a residue comprising 6'-N-ethylsisomicin (658 mg.) having the following physical constants: $[\alpha]_D^{26}$ + 148° (c, 1.0, MeOH); pmr (100 MHz, D$_2$O) δ1.16 (3H, t, J=8Hz, CH$_3$-CH$_2$), 1.20 (3H, s, CH$_3$-c), 2.53 (3H, s, N-Ch$_3$), 5.08 (1H, d, J=4Hz, H-1"), 5.36 (1H, d, J=2.5Hz, H-1') ppm; mass spectral peaks at n/e 476 (MH+), 475 (M+.), 430, 350, 332, 332, 304, 345, 327, 317, 309, 191, 173, 163, 145, 155, 160.

3. In the above procedure of Example 1A(1) by using as starting compound other tetra-N-alkanoylsisomicin derivatives in place of 1,3,2',3"-tetra-N-acetylsisomicin (e.g. 1,3,2',3"-tetra-N-propionylsisomicin or 1,3,2',3"-tetra-N-caprylylsisomicin) there is obtained the corresponding 1,3,2',3"-tetra-N-alkanoyl-6'-N-ethylsisomicin derivatives (e.g. 1,3,2',3"-tetra-N-propionyl-6'-N-ethylsisomicin or 1,3,2',3"-tetra-N-caprylyl-6'-N-ethylsisomicin), each of which, upon treatment with sodium hydroxide in the manner of Example 1A(2) yields 6'-N-ethylsisomicin.

B. In a manner similar to that described in Example 1A(1) treat each of the following poly-N-acetylaminoglycosides with acetaldehyde and sodium borohydride.
 1. 1,3,2',3"-tetra-N-acetylgentamicin C$_{1a}$,
 2. 1,3,3"-tri-N-acetylgentamicin B,
 3. 1,3,2',3"-tetra-N-acetyl-Antibiotic JI-20A,
 4. 1,3,2',3"-tetra-N-acetyl-Antibiotic 66-40B,
 5. 1,3,2',3"-tetra-N-acetyl-Antibiotic 66-40D,
 6. the 5-epi- and 5-epi-azido-5-deoxy- analogs of the foregoing,
 7. 1,3,5,2',3"-penta-N-acetyl-5-epi-amino-5-deoxygentamicin C$_{1a}$,
 8. 1,3,5,3"-tetra-N-acetyl-5-epi-amino-5-deoxy-gentamicin B,
 9. 1,3,5,2',3"-penta-N-acetyl-5-epi-amino-5-deoxy-Antibiotic JI-20A,
 10. 1,3,5,2', 3"-penta-N-acetyl-5-epi-amino-5-deoxysisomicin,
 11. 1,3,5,2',3"-penta-N-acetyl-5-epi-amino-5-deoxy-Antibiotic 66-40B,
 12. 1,3,5,2',3"-penta-N-acetyl-5-epi-amino-5-deoxy-Antibiotic 66-40D,
 13. 1,3,2',3"-tetra-N-acetyl-Antibiotic Mu-1,
 14. 1,3,2',3"-tetra-N-acetyl-Antibiotic Mu-2,
 15. 1,3,2',3"-tetra-N-acetyl-Antibiotic Mu-4, and
 16. 1,3,5,2',3"-penta-N-acetyl-Antibiotic Mu-5. Isolate and purify each of the resultant products in a manner similar to that described in Example 1A(1) to obtain, respectively,
 1. 1,3,2',3"-tetra-N-acetyl-6'-N-ethylgentamicin C$_{1a}$,
 b. 1,3,3"-tri-N-acetyl-6'-N-ethylgentamicin B,
 3. 1,3,2',3"-tetra-N-acetyl-6'-N-ethyl-Antibiotic JI-20A,
 4. 1,3,2',3"-tetra-N-acetyl-6'-N-ethyl-Antibiotic 66-40B,
 5. 1,3,2',3"-tetra-N-acetyl-6'-N-ethyl-Antibiotic 66-40D,
 6. the 5-epi- and the 5-epi-azido-5-deoxy- analogs of the foregoing,
 7. 1,3,5,2',3"-penta-N-acetyl-5-epi-amino-5-deoxy-6'-N-ethylgentamicin C$_{1a}$,
 8. 1,3,5,3"-tetra-N-acetyl-5-epi-amino-5-deoxy-6'-N-ethylgentamicin B,
 9. 1,3,5,2',3"-penta-N-acetyl-5-epi-amino-5-deoxy-6'-N-ethyl-Antibiotic JI-20A,
 10. 1,3,5,2',3"-penta-N-acetyl-5-epi-amino-5-deoxy-6'-N-ethylsisomicin,
 11. 1,3,5,2',3"-penta-N-acetyl-5-epi-amino-5-deoxy-6'-N-ethyl-Antibiotic 66-40B,
 12. 1,3,5,2',3"-penta-N-acetyl-5-epi-amino-5-deoxy-6'-N-ethyl-Antibiotic 66-40D,
 13. 1,3,2',3"-tetra-N-acetyl-6'-N-ethyl-Antibiotic Mu-1,
 14. 1,3,2',3"-tetra-N-acetyl-6'-N-ethyl-Antibiotic Mu-2,
 15. 1,3,2',3"-tetra-N-acetyl-6'-N-ethyl-Antibiotic Mu-4, and
 16. 1,3,5,2',3"-penta-N-acetyl-6'-N-ethyl-Antibiotic Mu-5. In a manner similar to that described in Example 1A(2) treat each of the foregoing poly-N-acetyl-6'-N-ethylaminoglycosides with sodium hydroxide at reflux temperature. Isolate and purify each of the resultant products in a manner similar to that described in Example 1A(2) to obtain, respectively,
 1. 6'-N-ethylgentamicin C$_{1a}$,
 2. 6'-N-ethylgentamicin B,
 3. 6'-N-ethyl-Antibiotic JI-20A,
 4. 6'-N-ethyl-Antibiotic 66-40B,
 5. 6'-N-ethyl-Antibiotic 66-40D,
 6. the 5-epi and the 5-epi-azido-5-deoxy analogs of the foregoing,
 7. 5-epi-amino-5-deoxy-6'-N-ethylgentamicin C$_{1a}$,
 8. 5-epi-amino-5-deoxy-6'-N-ethylgentamicin B,
 9. 5-epi-amino-5-deoxy-6'-N-ethyl-Antibiotic JI-20A,
 10. 5-epi-amino-5-deoxy-6'-N-ethylsisomicin,
 11. 5-epi-amino-5-deoxy-6'-N-ethyl-Antibiotic 66-40B,
 12. 5-epi-amino-5-deoxy-6'-N-ethyl-Antibiotic 66-40D,
 13. 6'-N-ethyl-Antibiotic Mu-1,
 14. 6'-N-ethyl-Antibiotic Mu-2,
 15. 6'-N-ethyl-Antibiotic Mu-4, and
 16. 6'-N-ethyl-Antibiotic Mu-5.

EXAMPLE 2
6'N-ISOPROPYLAMINOGYLCOSIDES

A. 6'-N-Isopropylsisomicin

1. In a manner similar to that described in Example 1A(1) treat 1,3,2',3"-tetra-N-acetylsisomicin (1.23 gms., 2 mmoles) with acetone (2.5 ml., 34 mmoles) and sodium borohydride (0.6 gms., 16 mmoles). Isolate and purify the resultant product in a manner similar to that described to obtain 1,3,2',3"-tetra-N-acetyl-6'-N-isopropylsisomicin; $[\alpha]_D^{26}$ + 188.8° (c, 0.2, H$_2$O); pmr (60 MHz, D$_2$O) δ 1.06, 1.08 (methyl groups), 1.96, 1.98, 2.02, 2.20 (12H, 4 × CH$_3$CON), 5.28 (1H, d, J=3.5Hz, H-1"), 5.52 (1H, d, J=2.5Hz, H-1') ppm; mass spectral peaks at m/e 657 (M+.), 485, 467, 457, 439, 424, 382, 275, 257, 247, 229, 211, 202.

2. In a manner similar to that described in Example 1A(2) treat 1,3,2',3"-tetra-N-acetyl-6'-N-isopropylsisomicin with 1 N sodium hydroxide at reflux temperature and isolate and purify the resultant product to obtain 6'-N-isopropylsisomicin; $[\alpha]_D^{26}$ + 163° (c,0.05, H$_2$O); pmr (60 MHz, D$_2$O) δ 1.17 (6H, d, J=6Hz, 2 × C-CH$_3$), 1.36 (3H, s, C-CH$_3$), 2.65 (3H, s, N-CH$_3$), 5.21 (1H, d, J=4Hz, H-1"), 5.45 (1H, d, J=3Hz, H-1') ppm; mass spectral peaks at m/e 489 (M $+^{i}$), 490 (MH)+, 359, 341, 331, 313, 350, 332, 322, 304, 169, 191, 173, 163, 145, 160.

B. In a manner similar to that described in above Example 2 A(1) treat each of the poly-N-acetylaminoglycoside starting compounds listed in Example 1B with acetone and sodium borohydride in methanol.

Isolate and purify each of the resultant products in a manner similar to that described to obtain, respectively,
1. 1,3,2,',3''-tetra-N-acetyl-6'-N-isopropylgentamicin C$_{1a}$,
2. 1,3,3''-tri-N-acetyl-6'-N-isopropylgentamicin B,
3. 1,3,2',3''-tetra-N-acetyl-6'-N-isopropyl-Antibiotic JI-20A,
4. 1,3,2',3''-tetra-N-acetyl-6'-N-isopropyl-Antibiotic 66-40B,
5. 1,3,2',3''-tetra-N-acetyl-6'-N-isopropyl-Antibiotic 66-40D,
6. the 5-epi- and the 5-epi-azido-5-deoxy- analogs of the foregoing,
7. 1,3,5,2',3''-penta-N-acetyl-5-epi-amino-5-deoxy-6'-N-isopropylgentamicin C$_{1a}$,
8. 1,3,5,3''-tetra-N-acetyl-5-epi-amino-5-deoxy-6'-N-isopropylgentamicin B,
9. 1,3,5,2',3''-penta-N-acetyl-5-epi-amino-5-deoxy-6'-N-isopropyl-Antibiotic JI-20A,
10. 1,3,5,2',3''-penta-N-acetyl-5-epi-amino-5-deoxy-6'-N-isopropylsisomicin,
11. 1,3,5,2',3''-penta-N-acetyl-5-epi-amino-5-deoxy-6'-N-isopropyl-Antibiotic 66-40B,
12. 1,3,5,2',3''-penta-N-acetyl-5-epi-amino-5-deoxy-6'-N-isopropyl-Antibiotic 66-40D,
13. 1,3,2',3''-tetra-N-acetyl-6'-N-isopropyl-Antibiotic Mu-1,
14. 1,3,2',3''-tetra-N-acetyl-6'-N-isopropyl-Antibiotic Mu-2,
15. 1,3,2',3''-tetra-N-acetyl-6'-N-isopropyl-Antibiotic Mu-4, and
16. 1,3,5,2',3''-penta-N-acetyl-6'-N-isopropyl-Antibiotic Mu-5.

Treat each of the foregoing poly-N-acetyl-6'-N-isopropylaminoglycosides with 1 N sodium hydroxide at reflux temperature in a manner similar to that described in above Example 2A(2) and isolate and purify each of the resulting products in a manner similar to that described to obtain, respectively,
1. 6'-N-isopropylgentamicin C$_{1a}$,
2. 6'-N-isopropylgentamicin B,
3. 6'-N-isopropyl-Antibiotic JI-20A,
4. 6'-N-isopropyl-Antibiotic 66-40B,
5. 6'-N-isopropyl-Antibiotic 66-40D,
6. the 5-epi- and the 5-epi-azido-5-deoxy- analogs of the foregoing,
7. 5-epi-amino-5-deoxy-6'-N-isopropyl-gentamicin C$_{1a}$,
8. 5-epi-amino-5-deoxy-6'-N-isopropyl-gentamicin B
9. 5-epi-amino-5-deoxy-6'-N-isopropyl-Antibiotic JI-20A,
10. 5-epi-amino-5-deoxy-6'-N-isopropyl-sisomicin,
11. 5-epi-amino-5-deoxy-6'-N-isopropyl-Antibiotic 66-40B,
12. 5-epi-amino-5-deoxy-6'-N-isopropyl-Antibiotic 66-40D,
13. 6'-N-isopropyl-Antibiotic Mu-1,
14. 6'-N-isopropyl-Antibiotic Mu-2,
15. 6'-N-isopropyl-Antibiotic Mu-4, and
16. 6'-N-isopropyl-Antibiotic Mu-5.

EXAMPLE 3

OTHER 6'-N-ALKYL AND 6'-N-ALKENYL AMINOGLYCOSIDES

A. Other 6'-N-alkyl and 6'-N-alkenylsisomicins

1. In the procedure of Example 1A(1) instead of acetaldehyde, substitute equivalent amounts of each of the following aldehydes:
1. 2-methyl-propanal,
2. n-pentanal,
3. 3-methylbutanal,
4. 2-methylbutanal,
5. 2,2-dimethylpropanal,
6. 2-ethylbutanal,
7. n-octanal,
8. propanal,
9. 2-ethyl-2-hexenal,
10. propanal,
11. n-butanal, and
12. cyclohexanecarboxaldehyde.

Isolate and purify each of the resultant products in a manner similar to that described in Example 1A(1) to obtain, respectively,
1. 1,3,2',3''-tetra-N-acetyl-6'-N-(β-methylpropyl)-sisomicin,
2. 1,3,2,',3''-tetra-N-acetyl-6''-N-(n-pentyl)sisomicin,
3. 1,3,2',3''-tetra-N-acetyl-6'-N-(γ-methylbutyl)-sisomicin
4. 1,3,2',3''-tetra-N-acetyl-6'-N-(β-methylbutyl)-sisomicin,
5. 1,3,2',3''-tetra-N-acetyl-6'-N-(β,β-dimethylpropyl)-sisomicin,
6. 1,3,2',3''-tetra-N-acetyl-6'-N-(β-ethylbutyl)-sisomicin,
7. 1,3,2',3''-tetra-N-acetyl-6'-N-(n-octyl)sisomicin,
8. 1,3,2',3''-tetra-N-acetyl-6'-N-(β-propenyl)sisomicin,
9. 1,3,2',3''-tetra-N-acetyl-6'-N-(β-ethyl-β-hexenyl)-sisomicin,
10. 1,3,2',3''-tetra-N-acetyl-6'--N-propylsisomicin,
11. 1,3,2',3''-tetra-N-acetyl-6'-N-(n-butyl)sisomicin, and
12. 1,3,2',3''-tetra-N-acetyl-6'-N-cyclohexylmethyl-sisomicin.

2. Treat each of the tetra-N-acetyl-6'-N-alkylsisomicin derivatives prepared in above Example 3A(1) with sodium hydroxide at reflux temperature and isolate each of the resultant products in a manner similar to that described in Example 1A(2) to obtain, respectively,
1. 6'-N-(β-methylpropyl)sisomicin,
2. 6'-N-(n-pentyl)sisomicin,
3. 6'-N-(γ-methylbutyl)sisomicin,
4. 6'-N-(β-methylbutyl)sisomicin,
5. 6'-N-(β,β-dimethylpropyl)sisomicin,
6. 6'-N-(β-ethylbutyl)sisomicin,
7. 6'-N-(n-octyl)sisomicin,
8. 6'-N-(β-propenyl)sisomicin,
9. 6'-N-(β-ethyl-β-hexenyl)sisomicin,
10. 6'-N-propylsisomicin,
11. 6'-N-(n-butyl)sisomicin, and
12. 6'-N-cyclohexylmethylsisomicin. B. (1) In the procedure of Example 3A(1) substitute for 1,3,2',3''-tetra-N-acetylsisomicin the following poly-N-acetyl aminoglycosides:
1. 1,3,2',3''-tetra-N-acetylgentamicin C$_{1a}$,
2. 1,3,3''-tri-N-acetylgentamicin B,
3. 1,3,2',3''-tetra-N-acetyl-Antibiotic JI-20A, 4. 1,3,2',3''-tetra-N-acetyl-Antibiotic 66-40B,
5. 1,3,2',3''-tetra-N-acetyl-Antibiotic 66-40D,
6. the 5-epi- and 5-epi-azido-5-deoxy- analogs of the foregoing,
7. 1,3,5,2',3''-penta-N-acetyl-5-epi-amino-5-deoxygentamicin $C_{1a}$,
8. 1,3,5,3''-tetra-N-acetyl-5-epi-amino-5-deoxygentamicin B,
9. 1,3,5,2',3''-penta-N-acetyl-5-epi-amino-5-deoxy-Antibiotic JI-20A,
10. 1,3,5,2',3''-penta-N-acetyl-5-epi-amino-5-deoxysisomicin,
11. 1,3,5,2',3''-penta-N-acetyl-5-epi-amino-5-deoxy-Antibiotic 66-, 40B,
12. 1,3,5,2',3''-penta-N-acetyl-5-epi-amino-5-deoxy-Antibiotic 66-40D,
13. 13,2',3''-tetra-N-acetyl-Antibiotic Mu-1,
14. 1,3,2',3''-tetra-N-acetyl-Antibiotic Mu-2,
15. 1,3,2',3''-tetra-N-acetyl-Antibiotic Mu-4, and
16. 1,3,5,2',3''-penta-N-acetyl-Antibiotic Mu-5.

Isolate and purify each of the resultant products in a manner similar to that described in Example 3A(1) to obtain the respective poly-N-acetyl-6'-N-alkyl derivatives of each of the above-listed aminoglycosides.

2. In a manner similar to that described in Example 1A(2) treat each of the poly-N-acetyl-6'-N-alkyl aminoglycoside derivatives prepared in above Example 3B(1) with 1 N sodium hydroxide at reflux temperature and isolate each of the resultant products to obtain, respectively, 1a. 6'-N-($\beta$-methylpropyl)gentamicin $C_{1a}$,
1b. 6'-N-(n-pentyl)gentamicin $C_{1a}$,
1c. 6'-N-($\gamma$-methylbutyl)gentamicin $C_{1a}$,
1d. 6'-N-($\beta$-methylbutyl)gentamicin $C_{1a}$,
1e. 6'-N-($\beta,\beta$-dimethylpropyl)gentamicin $C_{1a}$,
1f. 6'-N-($\beta$-ethylbutyl)gentamicin $C_{1a}$,
1g. 6'-N-(n-octyl)gentamicin $C_{1a}$,
1h. 6'-N-($\beta$-propenyl)gentamicin $C_{1a}$,
1i. 6'-N-($\beta$-ethyl-$\beta$-hexenyl)gentamicin $C_{1a}$,
1j. 6'-N-propylgentamicin $C_{1a}$,
1k. 6'-N-(n-butyl)gentamicin $C_{1a}$, and
1-l. 6'-N-cyclohexylmethylgentamicin $C_{1a}$,
2a. 6'-N-($\beta$-methylpropyl)gentamicin B,
2b. 6'-N-(n-pentyl)gentamicin B,
2c. 6'-N-($\gamma$-methylbutyl)gentamicin B,
2d. 6'-N-($\beta$-methylbutyl)gentamicin B,
2e. 6'-N-($\beta,\beta$-dimethylpropyl)gentamicin B,
2f. 6'-N-($\beta$-ethylbutyl)gentamicin B,
2g. 6'-N-(n-octyl)gentamicin B,
2h. 6'-N-($\beta$-propenyl)gentamicin B.
2i. 6'-N-($\beta$-ethyl-$\beta$-hexenyl)gentamicin B,
2j. 6'-N-propylgentamicin B,
2k. 6'-N-(n-butyl)gentamicin B, and
2-l. 6'-N-cyclohexylmethylgentamicin B;
3a. 6'-N-($\beta$-methylpropyl)-Antibiotic JI-20A,
3b. 6'-N-(n-pentyl)-Antibiotic JI-20A,
3c. 6'-N-($\gamma$-methylbutyl)-Antibiotic JI-20A,
3d. 6'-N-($\beta$-methylbutyl)-Antibiotic JI-20A,
3e. 6'-N-($\beta,\beta$-dimethylpropyl)-Antibiotic JI-20A,
3f. 6'-N-($\beta$-ethylbutyl)-Antibiotic JI-20A,
3g. 6'-N-(n-octyl)-Antibiotic JI-20A,
3h. 6'-N-($\beta$-propenyl)-Antibiotic JI-20A,
3i. 6'-N-($\beta$-ethyl-$\beta$-hexenyl)-Antibiotic JI-20A,
3j. 6'-N-propyl-Antibiotic JI-20A,
3k. 6'-N-(n-butyl)-Antibiotic JI-20A, and
3-l. 6'-N-cyclohexylmethyl-Antibiotic JI-20A;
4a. 6'-N-($\beta$-methylpropyl)-Antibiotic 66-40B,
4b. 6'-N-(n-pentyl)-Antibiotic 66-40B,
4c. 6'-N-($\gamma$-methylbutyl)-Antibiotic 66-40B,
4d. 6'-N-($\beta$-methylbutyl)-Antibiotic 66-40B,
4e. 6'-N-($\beta,\beta$-dimethylpropyl)-Antibiotic 66-40B,
4f. 6'-N-($\beta$-ethylbutyl)-Antibiotic 66-40B,
4g. 6'-N-(n-octyl)-Antibiotic 66-40B,
4h. 6'-N-($\beta$-propenyl)-Antibiotic 66-40B,
4i. 6'-N-($\beta$-ethyl-$\beta$-hexenyl)-Antibiotic 66-40B,
4j. 6'-N-propyl-Antibiotic 66-40B,
4k. 6'-N-(n-butyl)-Antibiotic 66-40B, and
4-l. 6'-N-cyclohexylmethyl-Antibiotic 66-40B;
5a. 6'-N-($\beta$-methylpropyl)-Antibiotic 66-40D,
5b. 6'-N-(n-pentyl)-Antibiotic 66-40D,
5c. 6'-N-($\gamma$-methylbutyl)-Antibiotic 66-40D,
5d. 6'-N-($\beta$-methylbutyl)-Antibiotic 66-40 D,
5e. 6'-N-($\beta,\beta$-dimethylpropyl)-Antibiotic 66-40D,
5f. 6'-N-($\beta$-ehtylbutyl)-Antibiotic 66-40D,
5g. 6'-N-(n-octyl)-Antibiotic 66-40D,
5h. 6'-N-($\beta$-propenyl)-Antibiotic 66-40D,
5i. 6'-N-($\beta$-ethyl-$\beta$-hexenyl)-Antibiotic 66-40 D,
5j. 6'-N-propyl-Antibiotic 66-40D,
5k. 6'-N-(n-butyl)-Antibiotic 66-40D, and
5-l. 6'-N-cyclohexylmethyl-Antibiotic 66-40D;
6. — 12. the 5-epi-, 5-epi-amino-5-deoxy- and 5-epiazido-5-deoxy analogs of the foregoing,
13a. 6'-N-($\beta$-methylpropyl)-Antibiotic Mu-1,
13b. 6'-N-(n-pentyl)-Antibiotic Mu-1,
13c. 6'-N-($\gamma$-methylbutyl)-Antibiotic Mu-1,
13d. 6'-N-($\beta$-methylbutyl)-Antibiotic Mu-1,
13e. 6'-N-($\beta,\beta$-dimethylpropyl)-Antibiotic Mu-1,
13f. 6'-N-($\beta$-ethylbutyl)-Antibiotic Mu-1,
13g. 6'-N-(n-octyl)-Antibiotic Mu-1,
13h. 6'-N-($\beta$-propenyl)-Antibiotic Mu-1,
13i. 6'-N-($\beta$-ethyl-$\beta$-hexenyl)-Antibiotic Mu-1,
13j. 6'-N-propyl-Antibiotic Mu-1,
13k. 6'-N-(n-butyl)-Antibiotic Mu-1, and
13-l. 6'-N-cyclohexylmethyl-Antibiotic Mu-1;
14a. 6'-N-($\beta$-methylpropyl)-Antibiotic Mu-2, Z
14b. 6'-N-(n-pentyl)-Antibiotic Mu-2,
14c. 6'-N-($\gamma$-methylbutyl)-Antibiotic Mu-2,
14d. 6'-N-($\beta$-methylbutyl)-Antibiotic Mu-2,
14e. 6'-N-($\beta,\beta$-dimethylpropyl)-Antibiotic Mu-2,
14f. 6'-N-($\beta$-ethylbutyl)-Antibiotic Mu-2, (14 g.) 6'-N-(n-octyl)-Antibiotic Mu-2,
14h. 6'-N-($\beta$-propenyl)-Antibiotic Mu-2,
14i. 6'-N-($\beta$-ethyl-$\beta$-hexenyl)-Antibiotic Mu-2,
14j. 6'-N-propyl-Antibiotic Mu-2,
14k. 6'-N-(n-butyl)-Antibiotic Mu-2, and
14-l. 6'-N-cyclohexylmethyl-Antibiotic Mu-2;
15a. 6'-N-($\beta$-methylpropyl)-Antibiotic Mu-4,
15b. 6'-N-(n-pentyl)-Antibiotic Mu-4,
15c. 6'-N-($\gamma$-methylbutyl)-Antibiotic Mu-4,
15d. 6'-N-($\beta$-methylbutyl)-Antibiotic Mu-4,
15e. 6'-N-($\beta,\beta$-dimethylpropyl)-Antibiotic Mu-4,
15f. 6'-N-($\beta$-ethylbutyl)-Antibiotic Mu-4,
15g. 6'-N-(n-octyl)-Antibiotic Mu-4,
15h. 6'-N-($\beta$-propenyl)-Antibiotic Mu-4,
15i. 6'-N-($\beta$-ethyl-$\beta$-hexenyl)-Antibiotic Mu-4,
15j. 6'-N-propyl-Antibiotic Mu-4,
15k. 6'-N-(n-butyl)-Antibiotic Mu-4, and
15-l. 6'-N-cyclohexylmethyl-Antibiotic Mu-4;
16a. 6'-N-($\beta$-methylpropyl)-Antibiotic Mu-5,
16b. 6'-N-(n-pentyl)-Antibiotic Mu-5,
16c. 6'-N-($\beta$-methylbutyl)-Antibiotic Mu-5,
16d. 6'-N-($\beta$-methylbutyl)-Antibiotic Mu-5,
16e. 6'-N-($\beta,\beta$-dimethylpropyl)-Antibiotic Mu-5,
16f. 6'-N-($\beta$-ethylbutyl)-Antibiotic Mu-5,
16g. 6'-N-(n-octyl)-Antibiotic Mu-5,
16h. 6'-N-($\beta$-propenyl)-Antibiotic Mu-5, 16i. 6'-N-(β-ethyl-β-hexenyl)-Antibiotic Mu-5,
16j. 6'-N-propyl-Antibiotic Mu-5,
16k. 6'-N-(n-butyl)-Antibiotic Mu-5, and
16-1. 6'-N-cyclohexylmethyl-Antibiotic Mu-5.

EXAMPLE 4 OTHER 6'-N-(HYDROXYALKYL)-AMINOGLYCOSIDES
A. 6'-N-(Hydroxyalkyl)-sisomicins 1. In the procedure of Example 1A(1), instead of acetaldehyde, substitute equivalent amounts of each of the following aldehydes:
1 5-hydroxypentanal,
2 2-hydroxypropanal,
b 3 2-hydroxy-3-methylbutanal,
4 2-hydroxy-2-methylpropanal,
5 4-hydroxybutanal,
6 8-hydroxyoctanal, and
7 2-hydroxy-4-pentenal. Isolate and purify each of the resultant products in a manner similar to that described in Example 1A(1) to obtain, respectively,
1. 1,3,2',3''-tetra-N-acetyl-6'-N-(ε-hydroxypentyl)-sisomicin,
2. 1,3,2',3''-tetra-N-acetyl-6'-N-(β-hydroxypropyl)-sisomicin,
3. 1,3,2',3''-tetra-N-acetyl-6'-N-(β-hydroxy-γ-methylbutyl)sisomicin,
4. 1,3,2',3''-tetra-N-acetyl-6'-N-(β-hydroxy-β-methylpropyl)sisomicin,
5. 1,3,2',3''-tetra-N-acetyl-6'-N-(δ-hydroxybutyl)-sisomicin,
6. 1,3,2',3''-tetra-N-acetyl-6'-N-(ε-hydroxyoctyl)-sisomicin,
7. 1,3,2',3''-tetra-N-acetyl-6'-N-(β-hydroxy-δ-pentenyl)sisomicin.

2. Treat each of the tetra-N-acetyl-6'-N-(hydroxyalkyl)sisomicin derivatives prepared in above Example 4A(1) with aqueous sodium hydroxide at reflux temperature and isolate each of the resultant products in a manner similar to that described in Example 1A(1) to obtain, respectively,
1. 6'-N-(ε-hydroxypentyl)sisomicin,
2. 6'-N-(β-hydroxypropyl)sisomicin,
3. 6'-N-(β-hydroxy-γ-methylbutyl)sisomicin,
4. 6'-N-(β-hydroxy-β-methylpropyl)sisomicin,
5. 6'-N-(δ-hydroxybutyl)sisomicin,
6. 6'-N-(ω-hydroxyoctyl)sisomicin,
7. 6'-N-(β-hydroxy-δ-pentenyl)sisomicin.

1. In the procedure of Example 4A(1), substitute for 1,3,2',3'''-tetra-N-acetylsisomicin each of the poly-N-acetylaminoglycosides prepared in Preparation 1C(2). Isolate and purify each of the resultant products in a manner similar to that described in Example 4A(1) to obtain the corresponding poly-N-acetyl-6'-N-(hydroxyalkyl)aminoglycoside derivative.

2. In a manner similar to that described in Example 1A(2) treat each of the poly-N-acetyl-6'-N-(hydroxyalkyl)aminoglycoside derivatives prepared in Example 4B(1) with 1 N sodium hydroxide at reflux temperature, and isolate each of the resultant products to obtain, respectively,
1a. 6'-N-(ε-hydroxypentyl)gentamicin $C_{1a}$,
1b. 6'-N-(β-hydroxypropyl)gentamicin $C_{1a}$,
1c. 6'-N-(β-hydroxy-γ-methylbutyl)gentamicin $C_{1a}$,
1d. 6'-N-(β-hydroxy-β-methylpropyl)gentamicin $C_{1a}$,
1e. 6'-N-(δ-hydroxybutyl)gentamicin $C_{1a}$,
1f. 6'-N-(ω-hydroxyoctyl)gentamicin $C_{1a}$,
1g. 6'-N-(β-hydroxy-δ-pentenyl)gentamicin $C_{1a}$,
2a. 6'-N-(ε-hydroxypentyl)gentamicin B,
2b. 6'-N-(β-hydroxypropyl)gentamicin B,
2c. 6'-N-(β-hydroxy-γ-methylbutyl)gentamicin B,
2d. 6'-N-(β-hydroxy-β-methylpropyl)gentamicin B,
2e. 6'-N-(δ-hydroxybutyl)gentamicin B,
2f. 6'-N-(ωhydroxypctul)gentamicin B,
2g. 6'-N-(ʃ-hydroxyoctyl)gentamicin B,
3a 6'-N-(ε-hydroxypentyl)-Antibiotic JI-20A,
3b 6'-N-(β-hydroxypropyl)-Antibiotic JI-20A,
3c 6'-N-(β-hydroxy-γ-methylbutyl)-Antibiotic JI-20A,
3d 6'-N-(β-hydroxy-β-methylpropyl)-Antibiotic JI-20A,
3e 6'-N-(δ-hydroxybutyl)-Antibiotic JI-20A,
3f 6'-N-(ω-hydroxyoctyl)-Antibiotic JI-20A,
3g 6'-N-(β-hydroxy-δ-pentenyl)-Antibiotic JI-20A,
4a. 6'-N-(ε-hydroxypentyl)-Antibiotic 66-40B,
4b. 6'-N-(β-hydroxypropyl)-Antibiotic 66-40B,
4c. 6'-N-(β-hydroxy-γ-methylbutyl)-Antibiotic 66-40B,
4d. 6'-N-(β-hydroxy-β-methylpropyl)-Antibiotic 66-40B,
4e. 6'-N-(δ-hydroxybutyl)-Antibiotic 66-40B,
4f. 6'-N-(ω-hydroxyoctyl)-Antibiotic 66-40B,
4g. 6'-N-(β-hydroxy-δ-pentenyl)-Antibiotic 66-40B,
p1 5a. 6'-N-(ε-hydroxypentyl)-Antibiotic 66-40D,
5b. 6'-N-(β-hydroxypropyl)-Antibiotic 66-40D,
5c. 6'-N-(β-hydroxy-γ-methylbutyl)-Antibiotic 66-40D,
5d. 6'-N-(β-hydroxy-β-methylpropyl)-Antibiotic 66-40D,
5e. 6'-N-(δ-hydroxybutyl)-Antibiotic 66-40D,
5f. 6'-N-(ω-hydroxyoctyl)-Antibiotic 66-40D,
5g. 6'-N-(β-hydroxy-δ-pentenyl()-Antibiotic 66-40D.
6. the 5-epi-, 5-epi-amino-5-deoxy-, and 5-epiazido-5-deoxy analogs of the foregoing,
7a. 6'-N-(ε-hydroxypentyl)-Antibiotic Mu-1,
7b. 6'-N-(β-hydroxypropyl()-Antibiotic Mu-1,
7c. 6'-N-(β-hydroxy-γ-methylbutyl)-Antibiotic Mu-1,
7d. 6'-N-(β-hydroxy-β-methylpropyl)-Antibiotic Mu-1,
7e. 6'-N-(δ-hydroxybutyl)-Antibiotic Mu-1,
7f. 6'-N-(ω-hydroxyoctyl)-Antibiotic Mu-1,
7g. 6'-N-(β-hydroxy-δ-pentenyl)-Antibiotic Mu-1,
8a. 6'-N-(ε-hydroxypentyl)-Antibiotic Mu-2,
8b. 6'-N-(β-hydroxypropyl)-Antibiotic Mu-2,
8c. 6'-N-(β-hydroxy-γ-methylbutyl)-Antibiotic Mu-2,
8d. 6'-N-(β-hydroxy-β-methylpropyl)-Antibiotic Mu-2,
8e. 6'-N-(δhydroxybutyl)-Antibiotic Mu-2,
8f. 6'-N-(ω-hydroxyoctyl)-Antibiotic Mu-2,
8g. 6'-N-(β-hydroxy-δ-pentenyl)-Antibiotic Mu-2,
9a. 6'-N-(ε-hydroxypentyl)-Antibiotic Mu-4,
9b. 6'-N-(β-hydroxypropyl)-Antibiotic Mu-4,
9c. 6'-N-(β-hydroxy-γ-methylbutyl)-Antibiotic Mu-4,
9d. 6'-N-(β-hydroxy-β-methylpropyl)-Antibiotic Mu-4,
9e. 6'-N-(δ-hydroxybutyl)-Antibiotic Mu-4,
9f. 6'-N-(ω-hydroxyoctyl)-Antibiotic Mu-4,
9g. 6'-N-(β-hydroxy-δ-pentenyl)-Antibiotic Mu-4, and
10a. 6'-N-(ε-hydroxypentyl)-Antibiotic Mu-5,
10b. 6'-N-(β-hydroxypropyl)-Antibiotic Mu-5,
10c. 6'-N-(β-hydroxy-γ-methylbutyl)-Antibiotic Mu-5,
10d. 6'-N-(β-hydroxy-β-methylpropyl)-Antibiotic Mu-5,
10e. 6'-N-(δ-hydroxybutyl)-Antibiotic Mu-5,
10f. 6'-N-(δ-hydroxyoctyl)-Antibiotic Mu-5, 10g. 6'-N-(β-hydroxy-δ-pentenyl)-Antibiotic Mu-5.

EXAMPLE 5
6'-N-(δ-AMINOBUTYL)AMINOGLYCOSIDES A. 6'-N-(δ-Aminobutyl)Sisomicin 1. In the procedure of Example 1A(1) instead of acetaldehyde substitute equivalent amounts of δ-acetamidobutyraldehyde. Isolate and purify the resultant products in a manner similar to that described in Example 1A(1) to obtain 1,3,2',3''-tetra-N-acetyl-6'-N-(δacetamidobutyl)sisomicin.

2. In a manner similar to that described in Example 1A(2) treat the 1,3,2',3''-tetra-N-acetyl-6'-N-(δ-acetamidobutyl)sisomicin of Example 5A(1) with 1 N sodium hydroxide at reflux temperature. Isolate and purify the resultant products in a manner similar to that described to obtain 6'-N-(δ-aminobutyl)sisomicin.

Alternately, the compound of this example is prepared according to procedures described in the following paragraphs 3 through 5.

3. In the procedure of Example 1A(1) instead of acetaldehyde use 4-phthalimidobutanal. Isolate and purify the resultant products in a manner similar to that described to obtain 1,3,2',3''tetra-N-acetyl-6'-N-(δ-phthalimidobutyl)sisomicin.

4. To 0.5 g. of 1,3,2',3''-tetra-N-acetyl-6'-N-(δ-phthalimidobutyl)sisomicin, add 5 ml. of 2 M methanolic hydrazine acetate and heat at 50° C for 15 hours. Pour the reaction solution into a large volume of tetrahydrofuran and collect by filtration the resultant precipitate comprising 1,3,2',,3''-tetra-N-acetyl-6'-N-(δ-aminobutyl)sisomicin.

5. In a manner similar to that described in Example 1A(2) treat 1,3,2',3''-tetra-N-acetyl-6'-N-(δ-aminobutyl)sisomicin with aqueous sodium hydroxide at reflux temperature. Isolate and purify the resultant product in a manner similar to that described in Example 1A(2) to obtain 6'-N-(δ-aminobutyl)sisomicin.

B. OTHER (δ-AMINOBUTYL)AMINOGLYCOSIDES

1. In a manner similar to that described in Example 5A(1) treat each of the poly-N-acetylaminoglycosides of Preparation 1C(2) with δ-acetamidobutyraldehyde in methanol followed by treatment with sodium borohydride. Isolate and purify each of the resultant products in a manner similar to that described in Example 5A(1) to obtain the corresponding poly-N-acetyl-6'-N-(δ-acetamidobutyl)-aminoglycoside.

2. In a manner similar to that described in Example 1A(2) treat each of the poly-N-acetyl derivatives prepared as described in Example 5B(1) with aqueous sodium hydroxide at reflux temperature. Isolate and purify each of the resultant products in a manner similar to that described to obtain, respectively,
   1. 6'-N-(δ-aminobutyl)gentamicin $C_{1a}$,
   2. 6'-N-(δ-aminobutyl)gentamicin B,
   3. 6'-N-(δ-aminobutyl)-Antibiotic JI-20A,
   4. 6'-N-(δ-aminobutyl)-Antibiotic 66-40B,
   5. 6'-N-(δ-aminobutyl)-Antibiotic 66-40D.
   6. the 5-epi-, 5-epi-N-acetylamino-5-deoxy- and 5-epi-azido-5-deoxy- analogs of the foregoing,
   7. 6'-N-(δ-aminobutyl)-Antibiotic Mu-1,
   8. 6'-N-(δaminobutyl)-Antibiotic Mu-2,
   9. 6'-N-(δ-aminobutyl)-Antibiotic Mu-4, and
   10. 6'-N-(δ-aminobutyl)-Antibiotic Mu-5.

EXAMPLE 6 OTHER 6'-N-(AMINOALKYL)AMINOGLYCOSIDES AND 6'-N-(HYDROXYAMINOALKYL)AMINOGLYCOSIDES A. 6'-N-(Aminoalkyl)Sisomicins and 6'-N-(Hydroxyaminoalkyl)Sisomicins 1. In the procedure of Example 1A(1) instead of acetaldehyde substitute equivalent quantities of each of the following amino substituted aldehydes:
   1. 3-phthalimidopropanal,
   2. 5-phthalimidopentanal,
   3. 2-phthalimidopropanal,
   4. 2-hydroxy-5-phthalimidopentanal,
   5. 3-methyl-3-hydroxy-4-phthalimidobutanal,
   6. 2-hydroxy-4-phthalimidobutanal,
   7. 2-phthalimido-3-methylbutanal,
   8. 2-hydroxy-3-phthalimidopropanal,
   9. 2-hydroxy-2-methyl-3-phthalimidopropanal, and
   10. 8-phthalimidooctanal.

Isolate and purify each of the resultant products in a manner similar to that described in Example 1A(1) to obtain, respectively,
1. 1,3,2',3''-tetra-N-acetyl-6'-N-(γ-phthalimidopropyl)sisomicin,
2. 1,3,2',3''-tetra-N-acetyl-6'-N-(ε-phthalimidopentyl)sisomicin,
3. 1,3,2',3''-tetra-N-acetyl-6'-N-(β-phthalimidopropyl)sisomicin,
4. 1,3,2',3''-tetra-N-acetyl-6'-N-(β-hydroxy-ε-phthalimidopentyl)sisomicin,
5. 1,3,2',3''-tetra-N-acetyl-6'-N-(γ-methyl-γ-hydroxy-δ-phthalimidobutyl)sisomicin,
6. 1,3,2',3''-tetra-N-acetyl-6'-N-(β-hydroxy-δ-phthalimidobutyl)sisomicin,
7. 1,3,2',3''-tetra-N-acetyl-6'-N-(β-phthalimido-γ-methylbutyl)sisomicin,
8. 1,3,2',3''-tetra-N-acetyl-6'-N-(β-hydroxy-γ-phthalimidopropyl)sisomicin,
9. 1,3,2',3''-tetra-N-acetyl-6'-N-(β-hydroxy-β-methyl-γ-phthalimidopropyl)sisomicin,
10. 1,3,2',3''-tetra-N-acetyl-6'-N-(ω-phthalimidooctyl)-sisomicin.

2. Treat each of the foregoing N-phthalimidoalkyl-sisomicin derivatives with methanolic hydrazine acetate as described in Example 5A(4) to obtain, respectively,
1. 1,3,2',3''-tetra-N-acetyl-6'-N-(γ-aminopropyl)sisomicin,
2. 1,3,2',3''-tetra-N-acetyl-6'-N-(ε-aminopentyl)sisomicin,
3. 1,3,2',3''-tetra-N-acetyl-6'-N-(β-aminopropyl)sisomicin,
4. 1,3,2',3''-tetra-N-acetyl-6'-N-(β-hydroxy-ε-aminopentyl)sisomicin,
5. 1,3,2',3''-tetra-N-acetyl-6'-N-(γ-methyl-γ-hydroxy-δ-aminobutyl)sisomicin,
6. 1,3,2',3''-tetra-N-acetyl-6'-N-(β-hydroxy-δ-aminobutyl)sisomicin,
7. 1,3,2',3''-tetra-N-acetyl-6'-N-(β-amino-γ-methylbutyl)sisomicin,
8. 1,3,2',3''-tetra-N-acetyl-6'-N-(β-hydroxy-γ-aminopropyl)sisomicin,
9. 1,3,2',3''-tetra-N-acetyl-6'-N-(β-hydroxy-β-methyl-γ-aminopropyl)sisomicin, and
10. 1,3,2',3''-tetra-N-acetyl-6'-N-(ω-aminooctyl)-sisomicin.

3. Treat each of the tetra-N-acetyl derivatives prepared in Example 6A(2) with aqueous sodium hydroxide at reflux temperature in a manner similar to that described in Example 1A(2) and isolate and purify each of the resultant products in a manner similar to that described to obtain, respectively, 1. 6'-N-(γ-aminopropyl)sisomicin,
2. 6'-N-(ε-aminopentyl)sisomicin,
3. 6'-N-(β-aminopropyl)sisomicin,
4. 6'-N-(β-hydroxy-ε-aminopentyl)sisomicin,
5. 6'-N-(γ-methyl-γ-hydroxy-δ-aminobutyl)sisomicin,
6. 6'-N-(β-hydroxy-δ-aminobutyl)sisomicin,
7. 6'-N-(β-amino-γ-methylbutyl)sisomicin,
8. 6'-N-(β-hydroxy-β-methyl-γ-aminopropyl)sisomicin, and
9. 6'-N-(β-hydroxy-β-methyl-γaminopropyl) sisomicin, and
10. 6'-N-(ω-aminooctyl)sisomicin.

B. 1. In the procedure of Example 6A(1) substitute for 1,3,2',3''-tetra-N-acetylsisomicin equivalent quantities of each of the poly-N-acetylaminoglycosides of Preparation 1C(2). Isolate and purify each of the resultant products in a manner similar to that described in Example 6A(1) to obtain the corresponding poly-N-acetyl-6'-N-(substituted alkyl) aminoglycoside derivatives.

2. Treat each of the N-phthalimidoalkyl aminoglycoside derivatives prepared in above Example 6A(1) with methanolic hydrazine acetate as described in Example 5A(4) to obtain the corresponding poly-N-acetyl-6'-N-(substituted alkyl) derivatives.

3. By treating each of the poly-N-acetyl derivatives of Example 6B(2) with 1 N sodium hydroxide at reflux temperature according to the procedure of Example 1A(2), there is obtained respectively, 1a. 6'-N-(γ-aminopropyl)gentamicin $C_{1a}$,
1b. 6'-N-(εaminopentyl) gentamicin $C_{1a}$,
1c. 6'-N-(βaminopropyl)gentamicin $C_{1a}$,
1d. 6'-N-(β-hydroxy-ε-aminopentyl)gentamicin $C_{1a}$,
1e. 6'-N-(γ-methyl-γ-hydroxy-δ-aminobutyl)gentamicin $C_{1a}$,
1f. 6'-N-(β-hydroxy-δ-aminobutyl)gentamicin $C_{1a}$,
1g. 6'-N-(β-amino-γ-methylbutyl)gentamicin $C_{1a}$,
1h. 6'-N-(β-hydroxy-γ-aminopropyl)gentamicin $C_{1a}$,
1i. 6'-N-(βhydroxy-β-methyl-γ-aminopropyl)gentamicin $C_{1a}$,
1j. 6'-N-(ω-aminooctyl)gentamicin $C_{1a}$.
2a. 6'-N-(γ-aminopropyl)gentamicin B,
2b. 6'-N-(ε-aminopentyl)gentamicin B,
2c. 6'-N-(β-aminopropyl)gentamicin B,
2d. 6'-N-(β-hydroxy-ε-aminopentyl)gentamicin B,
2e. 6'-N-(γ-methyl-γ-hydroxy-δ-aminobutyl)-gentamicin B,
2f. 6'-N-(β-hydroxy-δ-aminobutyl)gentamicin B,
2g. 6'-N-(β-amino-γ-methylbutyl)gentamicin B,
2h. 6'-N-(β-hydroxy-γ-aminopropyl)gentamicin B,
2i. 6'-N-hydroxy-β-methyl-γ-aminopropyl)-gentamicin B,
2j. 6'-N-(ω-aminooctyl)gentamicin B.
3a. 6'-N-(γ-aminopropyl)-Antibiotic JI-20A,
3b. 6'-N-(ε-aminopentyl)-Antibiotic JI-20A,
3c. 6'-N-(β-aminopropyl)-Antibiotic JI-20A,
3d. 6'-N-(β-hydroxy-ε-aminopentyl)-Antibiotic JI-20A,
3e. 6'-N-(γ-methyl-γ-hydroxy-δ-aminobutyl)-Antibiotic JI-20A,
3f. 6'-N-(β-hydroxy-δ-aminobutyl)-Antiobiotic JI-20A,
3g. 6'-N-(β-amino-γ-methylbutyl)-Antibiotic JI-20A,
3h. 6'-N-(β-hydroxy-γ-aminopropyl)-Antiobiotic JI-20A,
3i. 6'-N-(β-hydroxy-β-methyl-γ-aminopropyl)-Antibiotic JI-20A,
3j. 6'-N-(ω-aminooctyl)-Antibiotic JI-20A.
4a. 6'-N-(γ-aminopropyl)-Antibiotic 66-40B,
4b. 6'-N-(ε-aminopentyl)-Antibiotic 66-40B,
4c. 6'-N-(β-aminopropyl)-Antibiotic 66-40B,
4d. 6'-N-(β-hydroxy-ε-aminopentyl)-Antibiotic 66-40B,
4e. 6'-N-(γ-methyl-γ-hydroxy-δ-aminobutyl)-Antibiotic 66-40B,
4f. 6'-N-(β-hydroxy-δ-aminobutyl)-Antibiotic 66-40B,
4g. 6'-N-(β-amino-γ-methylbutyl)-Antibiotic 66-40B,
4h. 6'-N-(β-hydroxy-γ-aminopropyl)-Antibiotic 66-40B,
4i. 6'-N-(β-hydroxy-β-methyl-γ-aminopropyl)-Antibiotic 66-40B,
4j. 6'-N-(ω-aminooctyl)-Antibiotic 66-40B.
5a. 6'-N-(γ-aminopropyl)-Antibiotic 66-40D,
5b. 6'-N-(ε-aminopentyl)-Antibiotic 66-40D,
5c. 6'-N-(β-aminopropyl)-Antibiotic 66-40D,
5d. 6'-N-(β-hydroxy-ε-aminopentyl)-Antibiotic 66-40D,
5e. 6'-N-(γ-methyl-γ-hydroxy-δ-aminobutyl)-Antibiotic 66-40D,
5f. 6'-N-(β-hydroxy-δ-aminobutyl)-Antibiotic 66-40D,
5g. 6'-N-(β-amino-γ-methylbutyl)-Antibiotic 66-40D,
5h. 6'-N-(β-hydroxy-γ-aminopropyl)-Antibiotic 66-40D,
5i. 6'-N-(β-hydroxy-β-methyl-γ-aminopropyl)-Antibiotic 66-40D,
5j. 6'-N-(ω-aminooctyl)-Antibiotic 66-40D.
6. the 5-epi-, 5-epi-amino-5-deoxy-, and the 5-epi-azido-5-deoxy- analogs of the foregoing,
7a. 6'-N-(γ-aminopropyl)-Antibiotic Mu-1,
7b. 6'-N-(ε-aminopentyl)-Antibiotic Mu-1,
7c. 6'-N-(β-aminopropyl)-Antibiotic Mu-1,
7d. 6'-N-(β-hydroxy-ε-aminopentyl)-Antibiotic Mu-1,
7e. 6'-N-(γ-methyl-γ-hydroxy-δ-aminobutyl)-Antibiotic Mu-1,
7f. 6'-N-(β-hydroxy-δ-aminobutyl)-Antibiotic Mu-1,
7g. 6'-N-(β-amino-γ-methylbutyl)-Antibiotic Mu-1,
7h. 6'-N-(β-hydroxy-γ-aminopropyl)-Antibiotic Mu-1,
7i. 6'-N-(β-hydroxy-β-methyl-γ-aminopropyl)-Antibiotic Mu-1,
7j. 6'-N-(ω-aminooctyl)-Antibiotic Mu-1,
8a. 6'-N-(γ-aminopropyl)-Antibiotic Mu-2,
8b. 6'-N-(ε-aminopentyl)-Antibiotic Mu-2,
8c. 6'-N-(β-aminopropyl)-Antibiotic Mu-2,
8d. 6'-N-(β-hydroxy-ε-aminopentyl)-Antibiotic Mu-2,
8e. 6'-N-(γ-methyl-γ-hydroxy-δ-aminobutyl)-Antibiotic Mu-2,
8f. 6'-N-(β-hydroxy-δ-aminobutyl)-Antibiotic Mu-2,
8g. 6'-N-(β-amino-γ-methylbutyl)-Antibiotic Mu-2,
8h. 6'-N-(β-hydroxy-γ-aminopropyl)-Antibiotic Mu-2,
8i. 6'-N-(β-hydroxy-β-methyl-γ-aminopropyl)-Antibiotic Mu-2,
8j. 6'-N-(ω-aminooctyl)-Antibiotic Mu-2,
9a. 6'-N-(γ-aminopropyl)-Antibiotic Mu-4,
9b. 6'-N-(ε-aminopentyl)-Antibiotic Mu-4,
9c. 6'-N-(β-aminopropyl)-Antibiotic Mu-4,
9d. 6'-N-(β-hydroxy-ε-aminopentyl)-Antibiotic Mu-4,
9e. 6'-N-(γ-methyl-γ-hydroxy-δ-aminobutyl)-Antibiotic Mu-4,
9f. 6'-N-(β-hydroxy-δ-aminobutyl)-Antibiotic Mu-4, 9g. 6'-N-(β-amino-γ-methylbutyl)-Antibiotic Mu-4, 9h. 6'-N-(β-hydroxy-γ-aminopropyl)-Antibiotic Mu-4, 9i. 6'-N-(β-hydroxy-β-methyl-γ-aminopropyl)-Antibiotic Mu-4, 9j. 6'-N-(ω-aminooctyl)-Antibiotic Mu-4, 10a. 6'-N-(γ-aminopropyl)-Antibiotic Mu-5, 10b. 6'-N-(ε-aminopentyl)-Antibiotic Mu-5, 10c. 6'-N-(β-aminopropyl)-Antibiotic Mu-5, 10d. 6'-N-(β-hydroxy-ε-aminopentyl)-Antibiotic Mu-5, 10e. 6'-N-(γ-methyl-γ-hydroxy-δ-aminobutyl)-Antibiotic Mu-5, 10f. 6'-N-(β-hydroxy-δ-aminobutyl)-Antibiotic Mu-5, 10g. 6'-N-(β-amino-γ-methylbutyl)-Antibiotic Mu-5, 10h. 6'-N-(β-hydroxy-γ-aminopropyl)-Antiobiotic Mu-5, 10i. 6'-N-(β-hydroxy-β-methyl-γ-aminopropyl)-Antibiotic Mu-5, 10j. 6'-N-(ω-aminooctyl)-Antibiotic Mu-5.

C. 6'-N-Alkylaminoalkylsisomicins and 6'-N-Alkylaminohydroxyalkylsisomicins 1. 6'-N-(β-methylaminoethyl)sisomicin In the procedure of Example 1A(1) substitute 2-(N-methylacetamido)acetaldehyde for acetaldehyde. Isolate and purify the resultant product in a manner similar to that described in Example 1A(1) to obtain 6'-N-[β-(N-methylacetamido)ethyl]-sisomicin.

Treat the foregoing N-acetylated intermediate with 10% aqueous sodium hydroxide for 3 hours at 100° C. Pour the foregoing reaction solution onto Amberlite IRC-50 ion exchange resin, elute with 2 molar ammonium hydroxide, concentrate the combined eluates in vacuo to a volume of about 100 ml., then lyophilize to a residue comprising 6'-N-(β-methylaminoethyl)sisomicin.

2. In a manner similar to that described in Example 6C(1) treat sisomicin with 2-acetoxy-4-(N-methylacetamido)butanal. Isolate and purify the resultant product in a manner similar to that described in Example 1A(1) to obtain 6'-N-[δ-(N-methylacetamido)-β-acetoxy]butylsisomicin.

3. Treat the foregoing poly-N-acetyl derivative of Example 6C(2) with 1 N sodium hydroxide at reflux temperature according to the procedure of Example 6C(1) to obtain 6'-N-[δ-(N-methylamino)-β-hydroxy]-butylsisomicin.

D. (1) In the procedure of Example 6C(1) and 6C(2) substitute for 1,3,2',3''-tetra-N-acetylsisomicin, equivalent quantities of each of the poly-N-acetylaminoglycosides of Preparation 1C(2). Isolate and purify each of the resultant products in a manner similar to that described in Example 6C(1-3) to obtain the corresponding 6'-N-(β-methylaminoethyl) and 6'-N-[δ-(N-methylamino)-β-hydroxy]butyl derivatives.

EXAMPLE 7

ACID ADDITION SALTS

A. Sulfate Salts (Sulfuric Acid Addition Salts)

Dissolve 5.0 gm. of 6'-ethylsisomicin in 25 ml. of water and adjust the pH of the solution to 4.5 with 1N sulfuric acid. Pour into about 300 ml. of methanol with vigorous agitation, continue the agitation for about 10-20 minutes and filter. Wash the precipitate with methanol and dry at about 60° C in vacuo to obtain 6'-N-ethylsisomicin sulfate.

In like manner, the sulfate salt of the compounds of Examples 1 - 6 are also prepared.

B. Hydrochloride Salts

Dissolve 5.0 gm. of 6'-N-ethylsisomicin in 25 ml. of water. Acidify with 2N hydrochloric acid to pH 5. Lyophilize to obtain 6'-N-ethylsisomic in hydrochloride.

In like manner, the hydrochloride salt of the compounds of Examples 1 - 6 are also prepared.

The present invention includes within its scope pharmaceutical compositions comprising our novel 6'-N-X-4,6-di-O-(aminoglycosyl)-1,3-diaminocyclitol (X being as hereinabove defined for formula I) with a compatible, pharmaceutically acceptable carrier or coating. Also included within our invention is the method of eliciting an antibacterial response in a warm-blooded animal having a susceptible bacterial infection which comprises administering to said animal a non-toxic, antibacterially effective amount of a member selected from the group consisting of a 6'-N-alkylaminoglycoside derivative selected from the group consisting of 6'-N-X-sisomicin,
6'-N-X-Antibiotic 66-40B,
6'-N-X-Antibiotic 66-40D,
6'-N-X-Antibiotic Mu-1,
6'-N-X-Antibiotic Mu-2,
6'-N-X-Antiobiotic Mu-4,
6'-N-X-Antibiotic Mu-5, and the 5-epi-amino-5-deoxy-, and the 5-epi-azido-5-deoxy analogs of the following:

6'-N-X-gentamicin $C_{1a}$,
6'-N-X-gentamicin B,
6'-N-X-Antibiotic JI-20A,
6'-N-X-Antibiotic 66-40B,
6'-N-X-Antibiotic 66-40D, and
6'-N-X-sisomicin, wherein X is an alkyl substituent selected from the group consisting of alkyl, cycloalkylalkyl, alkenyl, hydroxyalkyl, aminoalkyl, alkylaminoalkyl, aminohydroxyalkyl and alkylaminohydroxyalkyl, said substituent having two to eight carbon atoms, the carbon in said substituent adjacent to the aminoglycoside nitrogen being primary or secondary and unsubstituted by hydroxyl or amino functions, and when said substituent is substituted by both hydroxyl and amino functions only one of said functions can be attached at any one carbon atom;

and the pharmaceutically acceptable acid addition salts thereof.

As discussed hereinabove, the 6'-N-X-4,6-di-O-(aminoglycosyl)-1,3-diaminocyclitols of this invention such as defined by formulae I–V and the non-toxic, pharmaceutically acceptable acid addition salts thereof are broad spectrum antibacterial agents which, advantageously, exhibit activity against organisms which are resistant to their 6'-N-unsubstituted precursors. Thus, the 6'-N-alkyl aminoglycosides of this invention can be used alone or in combination with other antibiotic agents to prevent the growth or reduce the number of bacteria various environments. They may be used, for example, to disinfect laboratory glassware, dental and medical equipment contaminated with *Staphylococcus aureus* or other bacteria inhibited by the 6'-N-alkyl derivatives of this invention. The activity of the 6'-N-X-4,6-di-O-(aminoglycosyl)-1,3-diaminocyclitols (X being as hereinabove defined for formula I) against gram negative bacteria renders them useful for combating infections caused by gram negative organisms, e.g. species of Proteus and Pseudomonas. Our 6'-N-X-4,6-di-O-(aminoglycosyl)-1,3-diaminocyclitols, e.g. 6'-N-X-sisomicin and 6'-N-X-gentamicin $C_{1a}$ (X being preferably ethyl) have veterinary applications, particularly in the treatment of mastitis in cattle and Salmonella induced diarrhea in domestic animals such as the dog and the cat.

In general, the dosage administered of the 6'-N-X-4,6-di-O-(aminoglycosyl)-1,3-diaminocyclitols will be dependent upon the age and weight of the animal species being treated, the mode of administration, and the type and severity of bacterial infection being prevented or reduced. In general, the dosage of 6'-N-X-4,6-di-O-(aminoglycosyl)-1,3-diaminocyclitols employed to combat a given bacterial infection will be similar to the dosage requirements of the corresponding 6'-N-unsubstituted 4,6-di-O-(aminoglycosyl)-1,3-diaminocyclitol precursor. Additionally, the 6'-N-X-4,6-di-O-(aminoglycosyl)-1,3-diaminocyclitols of formulae I–V, particularly those defined by formula I, e.g. 6'-N-X-sisomicin, are also advantageously cidal against certain gram negative organisms which are resistant to the 6'-N-unsubstituted precursors.

The 6'-N-X-4,6-di-O-(aminoglycosyl)-1,3-diaminocyclitols of formulae I–V and the pharmaceutically acceptable acid addition salts thereof may be administered orally. They may also be applied topically in the form of ointments, both hydrophillic and hydrophobic, in the form of lotions which may be aqueous, non-aqueous, or of the emulsion type or in the form of creams. Pharmaceutical carriers useful in the preparation of such formulations will include, for example such substances as water, oils, greases, polyesters, polyols and the like.

For oral administration the 6'-N-X-4,6-di-O-(aminoglycosyl) 1,3-diaminocyclitol antibacterials of this invention may be compounded in the form of tablets, capsules, elixirs or the like or may even be admixed with animal feed. It is in these dosage forms that the antibacterials are most effective for treating bacterial infections of the gastrointestinal tract which infections cause diarrhea.

In general, the topical preparations will contain from about 0.1 to about 3.0 gms. of 6'-N-X-4,6-O-(aminoglycosyl)-1,3-diaminocyclitols of formulae I–V per 100 gms. of ointment, creams or lotion. The topical preparations are usually applied gently to lesions from about 2 to about 5 times a day.

The antibacterials of this invention may be utilized in liquid form such as solutions, suspensions and the like for otic and optic use and may also be administered parenterally via intramuscular injection. The injectable solution or suspension will usually be administered at from about 1 mg. to about 10 mgs. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed:

Formulation I

| Tablet | 10 mg. Tab.* | 25 mg. Tab.* | 100 mg. tab.* |
|---|---|---|---|
| 6'-N-ethylsisomicin | 10.5 mg. | 26.25 mg. | 105.0 mg. |
| Lactose, impalpable powder | 197.50 mg. | 171.25 mg. | 126.00 mg. |
| Corn Starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

*5% excess

PROCEDURE

Prepare a slurry consisting of the 6'-N-ethylsisomicin lactose and polyvinylpyrrolidone. Spray dry the slurry. Add the corn starch and magnesium stearate. Mix and compress into tablets.

Formulation 2

| Ointment | |
|---|---|
| 6'-N-ethylsisomicin | 1.9 gm. |
| Methyl paraben U.S.P. | 0.5 gm. |
| Propyl paraben U.S.P. | 0.1 gm. |
| Petrolatum | to 1000 gm. |

PROCEDURE

1. Melt the petrolatum.
2. Mix the 5-epi-azido-5-deoxygentamicin $C_{1a}$, methylparaben and propylparaben with about 10% of the molten petrolatum.
3. Pass the mixture through a colloid mill.
4. Add the remainder of the petrolatum with agitation and cool the mixture until it becomes semi-solid. At this stage the product may be put into suitable containers.

Ointments of 6'-N-X-4,6-di-O-(aminoglycosyl)-1,3-diaminocyclitols of formula I–V (X being as hereinabove defined for formula I) and of the acid addition salts thereof are prepared by substituting an equivalent quantity of 6'-N-X-4,6-di-O-(aminoglycosyl)-1,3-diaminocyclitol (X being as hereinabove defined for formula I) or acid addition salt for 6'-N-ethylsisomicin in the foregoing example and by following substantially the procedure of the example.

Formulation 3

| Injectable Solution | Per 2.0 ml. vial* | per 50 liters* |
|---|---|---|
| 6'-N-ethylsisomicin sulfate | 8.4 mgs. | 21.00 gms. |
| Methyl paraben,U.S.P. | 3.6 mgs. | 90.0 gms. |
| Propyl paraben, U.S.P. | 0.4 mgs. | 10.0 gms. |
| Sodium bisulfite, U.S.P. | 6.4 mgs. | 160.0 gms. |
| Disodium Ethylenediamine tetracetate dihydrate, R.G. | 0.2 mgs. | 5.0 gms. |
| Water, U.S.P. q.s. | 2.0 ml. | 50.0 liters |

*Includes a 5% manufacturing overcharge.

PROCEDURE: FOR A 50.0 LITER BATCH

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25°–30° C by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the 6'-ethylsisomicin sulfate. Bring the batch volume up to 50.0 liters with water for injection and agitate until homogeneous.

Under sterile conditions, filter the solution through a suitable bacteria retentive filter collecting the filtrate in a filling tank.

Fill the filtrate aseptically into sterile pyrogenfree multiple dose vials, stopper and seal.

In like manner, injectable solutions of other 4,6-di-O-(aminoglycosyl)-1,3-diaminocyclitols and especially acid addition salts of such antibacterial agents, may be prepared by substituting an equivalent quantity of such compounds for 6'-N-ethyl-sisomicin sulfate and by following the procedure set forth above.

We claim:

1. A 6'-N-alkylaminoglycoside derivative selected from the group consisting of
   6'-N-X-sisomicin,
   6'-N-X-Antibiotic 66-40B,
   6'-N-X-Antibiotic 66-40D,
   6'-N-X-Antibiotic Mu-1,
   6'-N-X-antibiotic Mu-2,
   6'-N-X-Antibiotic Mu-4,
   6'-N-X-Antibiotic Mu-5, and
   the 5-epi-, 5-epi-amino-5-deoxy-, and the 5-epi-azido-5-deoxy-analogs of the following:
   6'-N-X-gentamicin $C_{1a}$
   6'-N-X-gentamicin B,
   6'-N-X-Antibiotic JI-20A,
   6'-N-X-Antibiotic 66-40B,
   6'-N-X-Antibiotic 66-40D, and
   6'-N-X-sisomicin,
   wherein X is a substituent selected from the group consisting of alkyl, cycloalkylalkyl, alkenyl, hydroxyalkyl, aminoalkyl, alkylaminoalkyl, aminohydroxyalkyl and alkylaminohydroxyalkyl, said substituent having two to eight carbon atoms, the carbon in said substituent adjacent to the aminoglycoside nitrogen being primary or secondary and unsubstituted by hydroxyl or amino functions, and when said substituent is substituted by both hydroxyl and amino functions only one of said functions can be attached at any one carbon atom;
   and the pharmaceutically acceptable acid addition salts thereof.

2. A compound of claim 1 wherein the substituent X has 2 to 4 carbon atoms.

3. A compound of claim 2 wherein X is ethyl.

4. A compound of claim 2 which is 6'-N-X-sisomicin.

5. A compound of claim 4 which is 6'-N-ethylsisomicin.

6. A compound of claim 4 which is 6'-N-isopropylsisomicin.

7. A compound of claim 4 which is 6'-(δ-aminobutyl)-sisomicin.

8. A 6'-N-X-aminoglycoside of claim 1 having all amino functions other than at 6' protected by a protecting group, Z, wherein X is as defined in claim 1 and Z is a member selected from the group consisting of a hydrocarboncarbonyl having up to 8 carbon atoms, benzyloxycarbonyl, and tert.-butoxycarbonyl.

9. A compound of claim 8 wherein X is ethyl and Z is acetyl.

10. A per-N-protected aminoglycoside selected from the group consisting of
    1,3,2',3''-tetra-N-Z-6'-N-Y-sisomicin,
    1,3,2',3''-tetra-N-Z-6'-N-Y-Antibiotic 66-40B,
    1,3,2',3''-tetra-N-Z-6'-N-Y-Antibiotic 66-40D,
    1,3,2',3''-tetra-N-Z-6'-N-Y-Antibiotic Mu-1,
    1,3,2',3''-tetra-N-Z-6'-N-Y-Antibiotic Mu-2,
    1,3,2',3''-tetra-N-Z-6'-N-Y-Antibiotic Mu-4,
    1,3,5,2',3''-penta-N-Z-6'-N-Y-Antibiotic Mu-5,
    1,3,5,2',3''-penta-N-Z-6'-N-Y-5-epi-amino-5-deoxy-gentamicin $C_{1a}$,
    1,3,5,3''-tetra-N-Z-6'-N-Y-5-epi-amino-5-deoxy-gentamicin B,
    1,3,5,2',3''-penta-N-Z-6'-N-Y-5-amino-5-deoxy-Antibiotic JI-20A,
    1,3,5,2',3''-penta-N-Z-6'-N-Y-5-epi-amino-5-deoxy-sisomicin,
    1,3,5,2',3''-penta-N-Z-6'-N-Y-5-epi-amino-5-deoxy-Antibiotic 66-40B,
    1,3,5,2',3''-penta-N-Z-6'-N-Y-5-epi-amino-5-deoxy-Antibiotic 66-40D; and
    the 5-epi- and 5-epi-azido-5-deoxy analogs of the following:
    1,3,2',3''-tetra-N-Z-6'-N-Y-gentamicin $C_{1a}$,
    1,3,3''-tri-N-Z-6'-N-Y-gentamicin B,
    1,3,2',3''-tetra-N-Z-6'-N-Y-Antibiotic JI-20A,
    1,3,2',3''-tetra-N-Z-6'-N-Y-sisomicin,
    1,3,2',3''-tetra-N-Z-6'-N-Y-Antibiotic 66-40B, and
    1,3,2',3''-tetra-N-Z-6'-N-Y-Antibiotic 66-40D,
    wherein Y is a member selected from the group consisting of trifluoroacetyl, benzyloxycarbonyl and tert.-butoxy-carbonyl;
    Z is a member selected from the group consisting of a hydrocarboncarbonyl having up to 8 carbon atoms, benzyloxycarbonyl, and tert.-betoxycarbonyl with the proviso that in a given compound Y and Z are different, with Z being a group which remains intact under conditions in which Y is removed.

11. A compound of claim 10 wherein Y is trifluoroacetyl and Z is acetyl.

12. A 6'-N-unsubstituted-poly-N-protected aminoglycoside selected from the group consisting of
    1,3,2',3''-tetra-N-Z-sisomicin,
    1,3,2',3''-tetra-N-Z-Antibiotic 66-40B,
    1,3,2',3''-tetra-N-Z-Antibiotic 66-40D,
    1,3,2',3''-tetra-N-Z-Antibiotic Mu-1,
    1,3,2',3''-tetra-N-Z-Antibiotic Mu-2,
    1,3,2',3''-tetra-N-Z-Antibiotic Mu-4,
    1,3,5,2',3''-penta-N-Z-Antibiotic Mu-5,
    1,3,5,2',3''-penta-N-Z-5-epi-amino-5-deoxygentamicin $C_{1a}$,
    1,3,5,3''-tetra-N-Z-5-epi-amino-5-deoxygentamicin B,
    1,3,5,2',3''-penta-N-Z-5-epi-amino-5-deoxy-Antibiotic JI-20A,
    1,3,5,2',3''-penta-N-Z-5-epi-amino-5-deoxysisomicin,
    1,3,5,2',3''-penta-N-Z-5-epi-amino-5-deoxy-Antibiotic 66-40B, and
    1,3,5,2',3''-penta-N-Z-5-epi-amino-5-deoxy-Antibiotic 66-40D;
    the 5-epi- and 5-epi-azido-5-deoxy- analogs of the following:
    1,3,2',3''-tetra-N-Z-gentamicin $C_{1a}$,
    1,3,3''-tri-N-Z-gentamicin B,
    1,3,2',3''-tetra-N-Z-Antibiotic JI-20A,
    1,3,2',3''-tetra-N-Z-sisomicin,
    1,3,2',3''-tetra-N-Z-Antibiotic 66-40B, and
    1,3,2',3''-tetra-N-Z-Antibiotic 66-40D,
    wherein Z is a hydrocarboncarbonyl having up to 8 carbon atoms, benzyloxycarbonyl, or tert.-butoxycarbonyl.

13. A compound of claim 12 wherein Z is acetyl.

14. The method of eliciting an antibacterial response in a warm-blooded animal having a susceptible bacterial infection, which comprises administering to said animal a non-toxic, antibacterially effective amount of a member selected from the group consisting of a 6'-N-alkylaminoglycoside derivative selected from the group consisting of
- 6'-N-X-sisomicin,
- 6'-N-X-Antibiotic 66-40B,
- 6'-N-X-Antibiotic 66-40D,
- 6'-N-X-Antibiotic Mu-1,
- 6'-N-X-Antibiotic Mu-2,
- 6'-N-X-Antibiotic Mu-4,
- 6'-N-X-Antibiotic Mu-5, and
- the 5-epi-, 5-epi-amino-5-deoxy-, and the 5-epi-azido-5-deoxy- analogs of the following:
- 6'-N-X-gentamicin $C_{1a}$
- 6'-N-X-gentamicin B,
- 6'-N-X-Antibiotic JI-20A,
- 6'-N-X-Antibiotic 66-40B,
- 6'-N-X-Antibiotic 66-40D, and
- 6'-N-X-sisomicin,
- wherein X is a substituent selected from the group consisting of alkyl, cycloalkylalkyl, alkenyl, hydroxyalkyl, aminoalkyl, alkylaminoalkyl, aminohydroxyalkyl and alkylaminohydroxyalkyl, said substituent having two to eight carbon atoms, the carbon in said substituent adjacent to the aminoglycoside nitrogen being primary or secondary and unsubstituted by hydroxyl or amino functions, and when said substituent is substituted by both hydroxyl and amino functions only one of said functions can be attached at any one carbon atom;
- and the pharmaceutically acceptable acid addition salts thereof.

15. A pharmaceutical composition comprising an antibacterially effective amount of a compound selected from the group consisting of
- 6'-N-X-sisomicin,
- 6'-N-X-Antibiotic 66-40B,
- 6'-N-X-Antibiotic 66-40D,
- 6'-N-X-Antibiotic Mu-1,
- 6'-N-X-Antibiotic Mu-2,
- 6'-N-X-Antibiotic Mu-4,
- 6'-N-X-Antibiotic Mu-5, and
- the 5-epi-, 5-epi-amino-5-deoxy-, and the 5-epi-azido-5-deoxy- analogs of the following:
- 6'-N-X-gentamicin $C_{1a}$
- 6'-N-X-gentamicin B,
- 6'-N-X-Antibiotic JI-20A,
- 6'-N-X-Antibiotic 66-40B,
- 6'-N-X-Antibiotic 66-40D, and 6'-N-X-sisomicin,
- wherein x is a substituent selected from the group consisting of alkyl, cycloalkylalkyl, alkenyl, hydroxyalkyl, aminoalkyl, alkylaminoalkyl, aminohydroxyalkyl and alkylaminohydroxyalkyl, said substituent having two to eight carbon atoms, the carbon in said substituent adjacent to the aminoglycoside nitrogen being primary or secondary and unsubstituted by hydroxyl or amino functions, and when said substituent is substituted by both hydroxyl and amino functions only one of said functions can be attached at any one carbon atom;
- and the pharmaceutically acceptable acid addition salts thereof,
- together with a non-toxic pharmaceutically acceptable carrier.

* * * * *

UNITED STATES PATENT OFFICE
CERTIFICATE OF CORRECTION

Patent No. 4,044,123    Dated August 23, 1977

Inventor(s) Peter J. L. Daniels et al    Page 1 of 2

It is certified that error appears in the above-identified patent and that said Letters Patent are hereby corrected as shown below:

Column 1, line 39, "-6'-alkylaminoalkyl," should read ---6'-$\underline{N}$-alkylaminoalkyl,---. Column 4, line 65, "-6'-alkylgentamicins" should read ---6'-$\underline{N}$-alkylgentamicins---. Column 10, line 12, "in form" should read ---to form---; line 66, "branched and chain alkyl" should read ---branched chain alkyl---. Column 16, line 19, "B. 6'-Trifluoroacetyl-" should read ---B. 6'-$\underline{N}$-Trifluoroacetyl---. Column 19, line 66, "-5-N-propionyl " should read ---5-epi-$\underline{N}$-propionyl---. Column 21, line 3, "-N-Ch$_3$)," should read ---N-CH$_3$), line 5, "at n/e 476" should read ---at m/e 476---. Column 22, line 62, "489 (M + 1)" should read ---489 (M$^+$)---. Column 24, line 17, "8. propanal" should read --- 8, propenal---; line 27, "-acetyl-6"-N-" should read ---acetyl-6'-$\underline{N}$---. Column 26, line 63, "-($\beta$-methylbutyl)-" should read ---($\gamma$-methylbutyl)---. Column 27, line 14, "b 3 2-hydroxy-" should read --- 3, 2-hydroxy---. Column 28, line 5, "-($\omega$hydroxypctul)-" should read ---($\omega$-hydroxyoctyl)---; line 6, "-($\int$ hydroxyoctyl)-" should read ---($\beta$-hydroxy-$\delta$-pentenyl)---; line 68, "-($\delta$-hydroxyoctyl)-" should read ---($\omega$-hydroxyoctyl)---. Column 31, line 12, "-($\beta$-hydroxy-$\beta$-methyl-$\gamma$-aminopropyl)-" should read ---($\beta$-hydroxy-$\gamma$-aminopropyl)---. Column 36, lines 2-4, "10 mg. Tab.   25 mg. Tab.   100 mg. Tab.
   10.5 mg.*      26.25 mg.*     105.0 mg.*    "
should read ---10 mg. Tab.   25 mg. Tab.   100 mg. Tab.
   10.5* mg.      26.25* mg.     105.0* mg. ---.

UNITED STATES PATENT OFFICE
CERTIFICATE OF CORRECTION

Patent No. 4,064,123        Dated August 23, 1977

Inventor(s) Peter J. L. Daniels et al      Page 2 of 2

It is certified that error appears in the above-identified patent and that said Letters Patent are hereby corrected as shown below:

Column 36, lines 46-48, "Per 2.0 ml. Vial * / 8.4 mgs.   Per 50 liters * / 21.00 gms." should read ---Per 2.0 ml. Vial / 8.4* mgs.   Per 50 Liters / 21.00* gms. ---.

Column 36, line 68, "the 6'-ethyl" should read ---the 6'-$\underline{N}$-ethyl---.

Column 37, lines 53 and 54, change "6'-($\delta$-aminobutyl)sisomicin" to "6'-$\underline{N}$-($\delta$-aminobutyl)sisomicin".

Signed and Sealed this

Seventeenth Day of January 1978

[SEAL]

Attest:

RUTH C. MASON        LUTRELLE F. PARKER
*Attesting Officer*        *Acting Commissioner of Patents and Trademarks*